United States Patent
Bilotti et al.

(10) Patent No.: US 8,006,701 B2
(45) Date of Patent: Aug. 30, 2011

(54) DEVICE AND METHOD FOR THE THERAPY OF OBESITY

(75) Inventors: Federico Bilotti, Via Padre G.A. (IT); Michele D'Arcangelo, Via Benedetto Croce (IT); Roberto Tacchino, Viale Della Tecnica (IT); Jesse J. Kuhns, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 313 days.

(21) Appl. No.: 11/662,029

(22) PCT Filed: Jun. 17, 2005

(86) PCT No.: PCT/IT2005/000348
§ 371 (c)(1),
(2), (4) Date: Aug. 18, 2008

(87) PCT Pub. No.: WO2006/048905
PCT Pub. Date: May 11, 2006

(65) Prior Publication Data
US 2008/0302855 A1    Dec. 11, 2008

(30) Foreign Application Priority Data
Nov. 5, 2004  (IT) .......................... MI2004A002132

(51) Int. Cl.
*A61B 17/11* (2006.01)
*A61B 17/04* (2006.01)

(52) U.S. Cl. .... 128/898; 227/19; 227/175.1; 227/175.2; 227/180.1; 227/179.1

(58) Field of Classification Search ............... 227/179.1, 227/175.1, 175.2, 180.1; 128/898
See application file for complete search history.

(56) References Cited

U.S. PATENT DOCUMENTS

| | | | | |
|---|---|---|---|---|
| 4,848,367 A * | 7/1989 | Avant et al. | 128/898 |
| 4,917,114 A * | 4/1990 | Green et al. | 227/179.1 |
| 5,104,025 A * | 4/1992 | Main et al. | 227/175.1 |
| 5,205,459 A * | 4/1993 | Brinkerhoff et al. | 227/179.1 |
| 5,222,963 A * | 6/1993 | Brinkerhoff et al. | 606/153 |
| 5,250,058 A * | 10/1993 | Miller et al. | 606/154 |
| 5,275,322 A * | 1/1994 | Brinkerhoff et al. | 227/175.1 |
| 5,292,053 A * | 3/1994 | Bilotti et al. | 227/179.1 |
| 5,309,927 A * | 5/1994 | Welch | 128/898 |
| 5,327,914 A * | 7/1994 | Shlain | 128/898 |
| 5,355,897 A * | 10/1994 | Pietrafitta et al. | 128/898 |
| 5,829,447 A * | 11/1998 | Stevens et al. | 128/898 |
| 5,855,614 A * | 1/1999 | Stevens et al. | 128/898 |
| 5,924,424 A * | 7/1999 | Stevens et al. | 128/898 |
| 5,951,576 A * | 9/1999 | Wakabayashi | 606/151 |
| 6,102,271 A * | 8/2000 | Longo et al. | 227/180.1 |
| 6,110,187 A * | 8/2000 | Donlon | 606/151 |
| 6,338,737 B1 * | 1/2002 | Toledano | 606/219 |
| 6,482,224 B1 | 11/2002 | Michler et al. | |
| 6,503,259 B2 * | 1/2003 | Huxel et al. | 606/153 |
| 6,679,268 B2 * | 1/2004 | Stevens et al. | 128/898 |
| 6,981,979 B2 * | 1/2006 | Nicolo | 606/153 |

(Continued)

*Primary Examiner* — Brian D Nash

(57) ABSTRACT

An anastomotic device, particularly a circular stapler (10), comprises a handle (12) and a stem (14). A channel suitable to receive a guide wire at least partially develops along the length of the stapler. The stem (14) is made of a flexible material, such as to facilitate reaching the site requiring anastomosis. The circular stapler (10) comprises an anvil (16) suitable to be introduced on the free end of the stem (14). The anvil (16) comprises a channel (22) suitable to receive a guide wire (66) and extending along the anvil, and a portion (20) suitable to act as a striker against the wall of one of the portions (A; B) of the tissues to be joined.

6 Claims, 25 Drawing Sheets

U.S. PATENT DOCUMENTS

| | | |
|---|---|---|
| 7,059,331 B2 * | 6/2006 | Adams et al. .................. 128/898 |
| 2002/0068947 A1 * | 6/2002 | Kuhns et al. ................... 606/143 |
| 2003/0178465 A1 * | 9/2003 | Bilotti et al. ................ 227/180.1 |

* cited by examiner

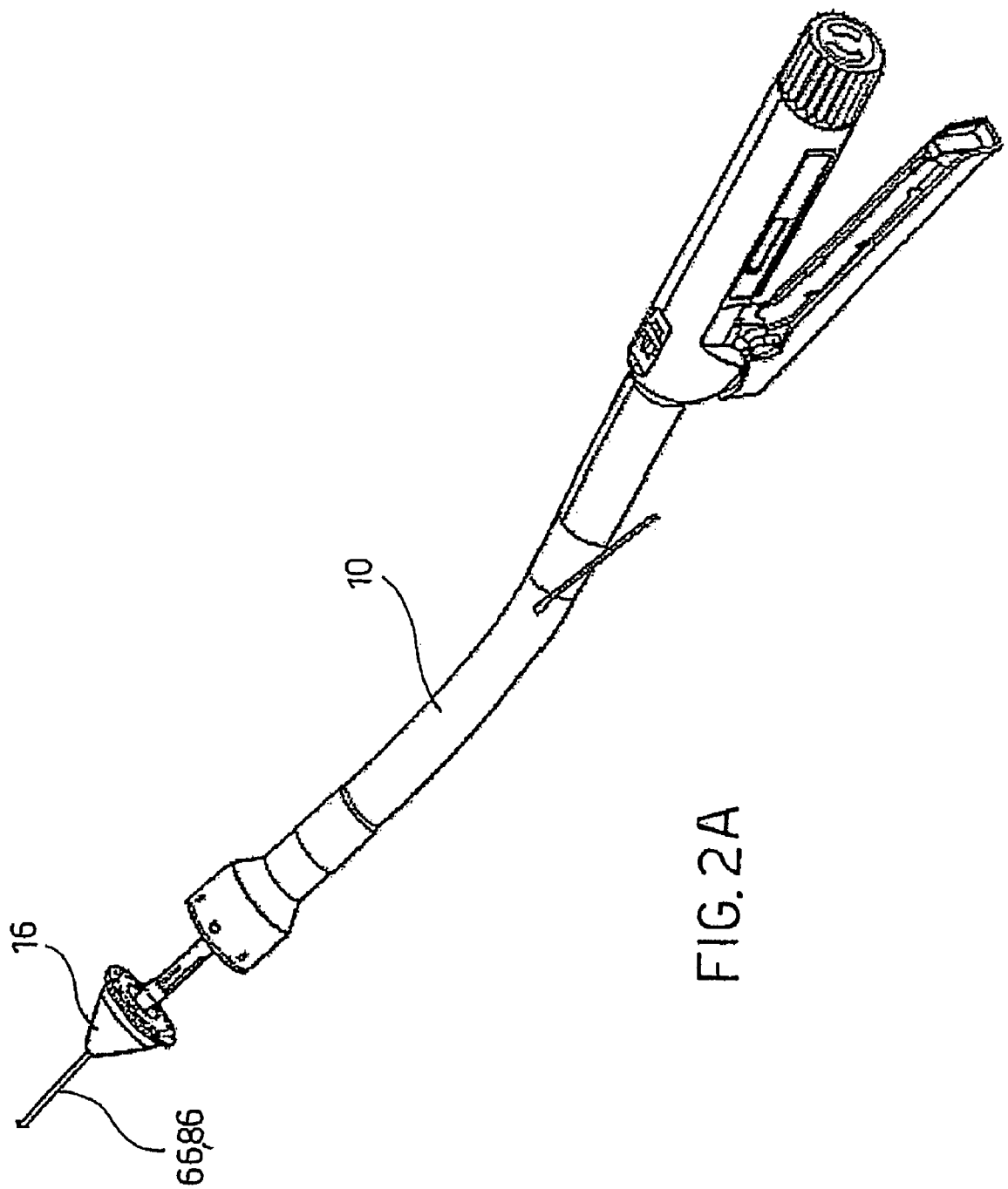

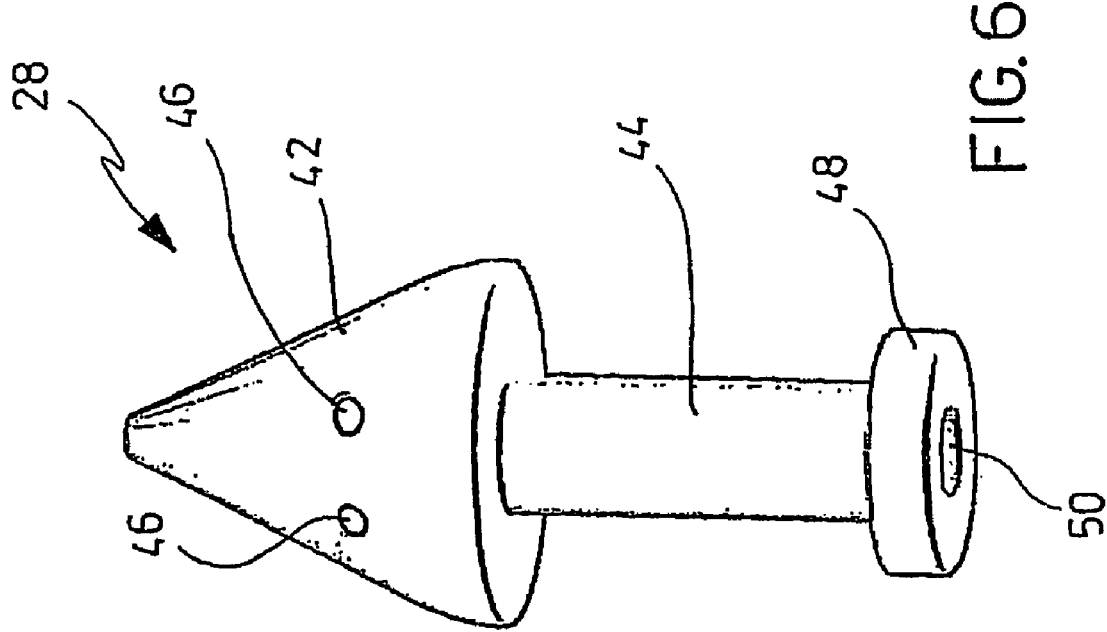
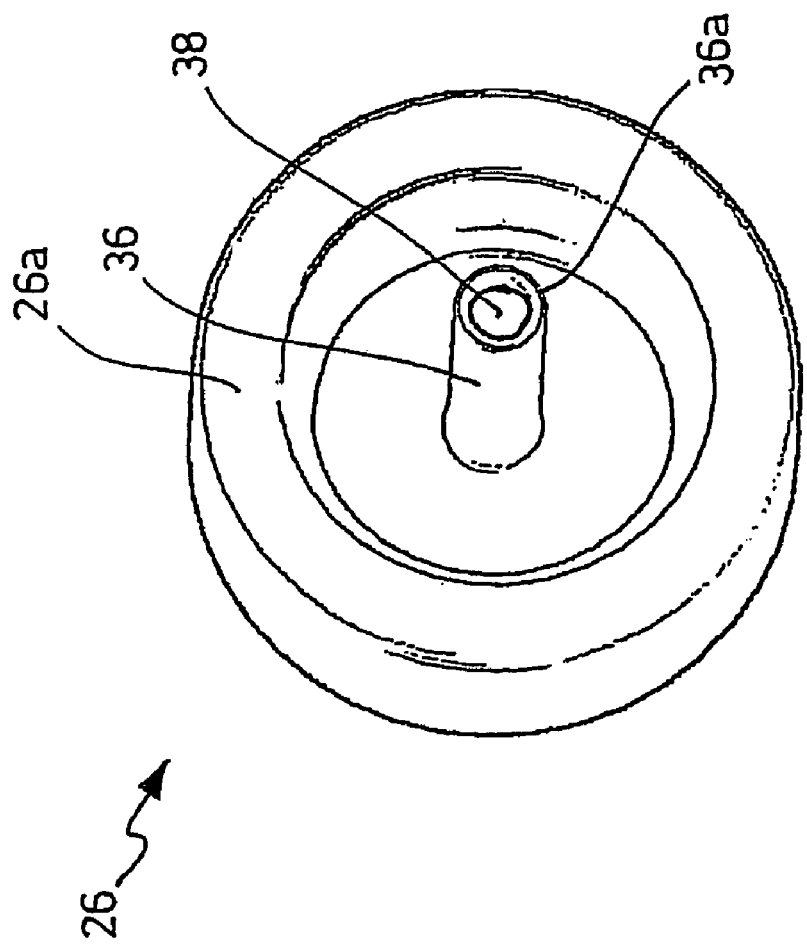

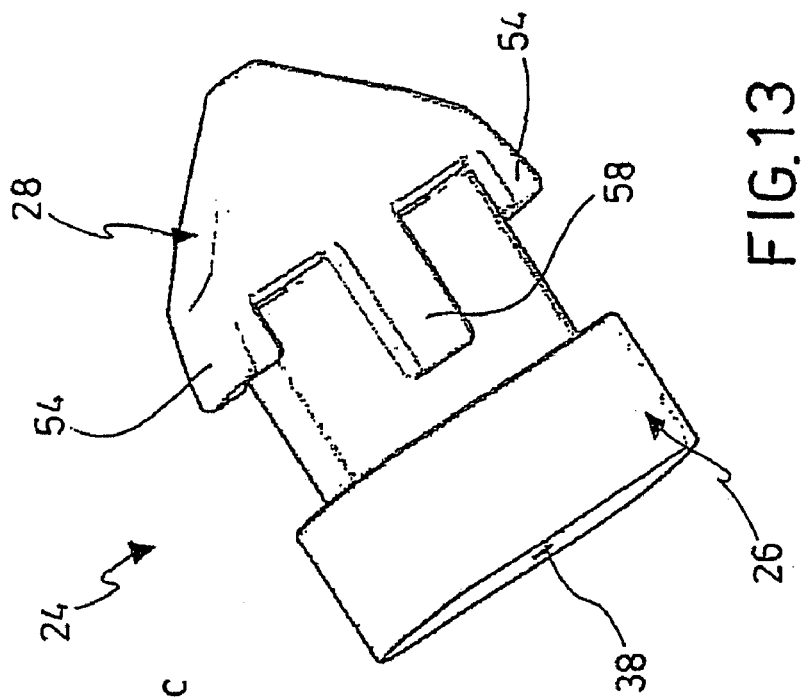
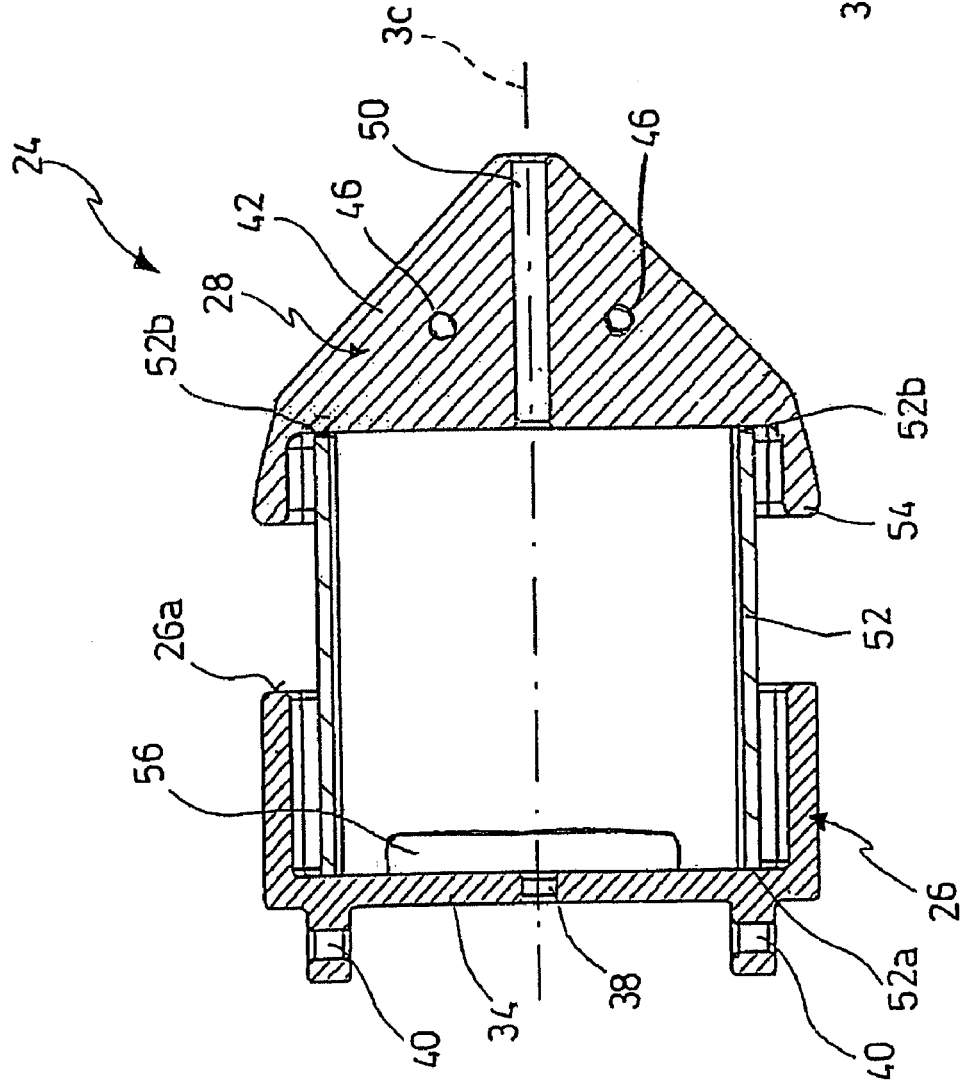
FIG. 13
FIG. 14

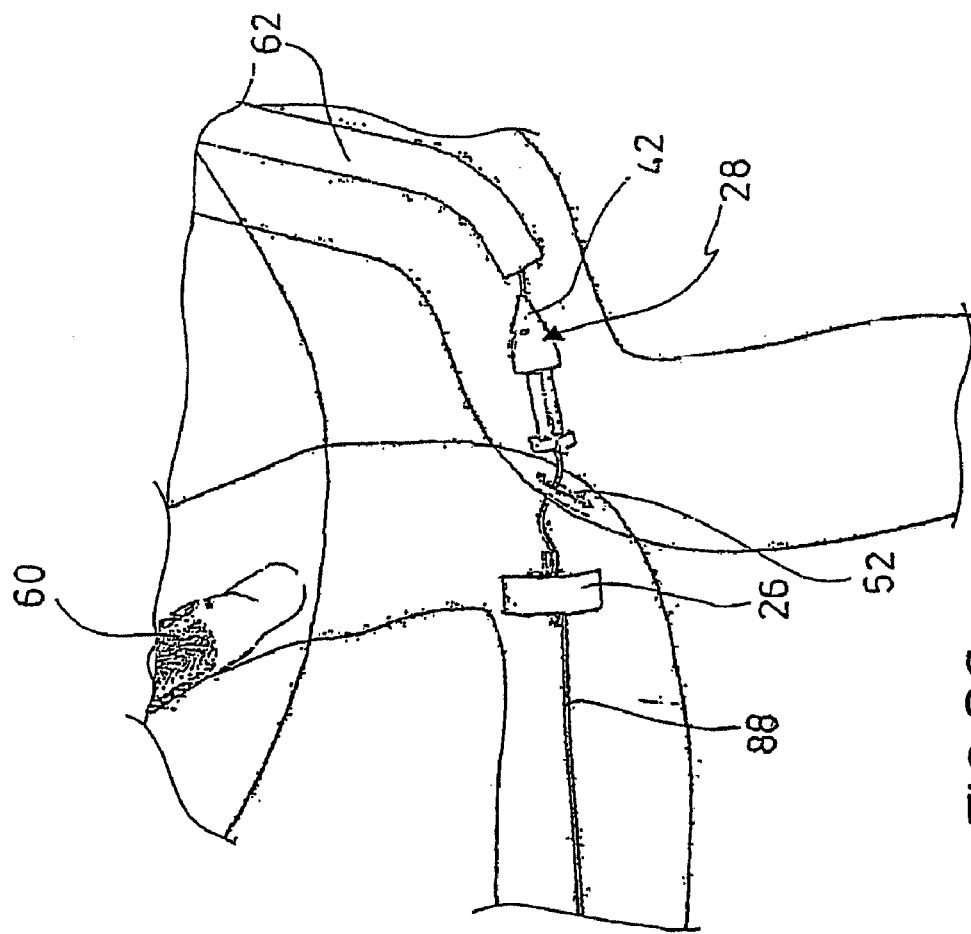
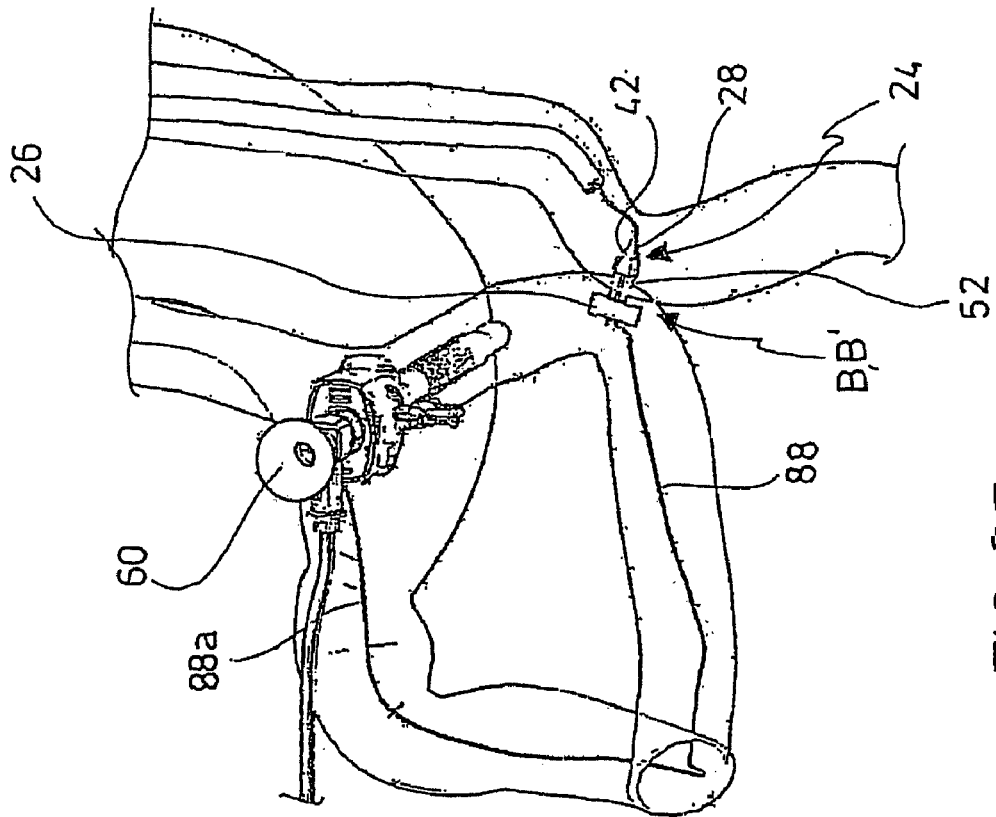
FIG. 35
FIG. 36

DEVICE AND METHOD FOR THE THERAPY OF OBESITY

The present invention relates to devices and methods for the therapy of obesity in general. Particularly, the present invention relates to devices for drawing together tissues that are suitable to be used in a method for carrying out anastomosis in tracts of the digestive tube.

According to a further aspect, the present invention relates to a circular stapler, which is also particularly suitable to be used in a method for carrying out anastomosis in tracts of the digestive tube.

The present invention further relates to a method for carrying out anastomosis in tracts of the digestive tube.

At present, surgical anastomoses are very difficult to carry out via endoluminal access. Most of anastomoses, in fact, are created by using open or laparoscopic surgical techniques.

Accordingly, no effective surgical instruments are available which offer the guide and control required to suitably drawing together the tissue surfaces and/or connecting the surfaces with a passage (anastomosis) through the body cavities.

The problem at the heart of the present invention is to provide devices capable of drawing tissues together and create a passage therebetween. A further problem at the heart of the present invention is to provide devices capable of being used in a method for carrying out anastomosis in tracts of the digestive tube with endoluminal access.

This problem is solved by means of a circular stapler according to claim 1.

According to a still further aspect, a problem at the heart of the present invention is to provide a method for carrying out anastomoses in tracts of the digestive tube with endoluminal access.

BRIEF DESCRIPTION OF THE DRAWINGS

Further characteristics and advantages of the devices, circular stapler and method according to the invention will result from the description below of preferred exemplary embodiments, which are given as a non-limiting indication, with reference to the attached figures, wherein:

FIG. 2a illustrates a perspective view of the stapler from FIG. 1, guide wire and device from FIG. 2 during an assembly step for performing a suture;

FIG. 5 illustrates a perspective view of a detail of the device from FIG. 3;

FIG. 6 illustrates a perspective view of a detail of the device from FIG. 3;

FIG. 13 illustrates a perspective view of a possible embodiment of a positioning device;

FIG. 14 illustrates a sectional view along a plane containing a longitudinal axis of the device from FIG. 13;

FIG. 17-40 illustrate several steps of a method according to the present invention;

DETAILED DESCRIPTION

Figure 1:
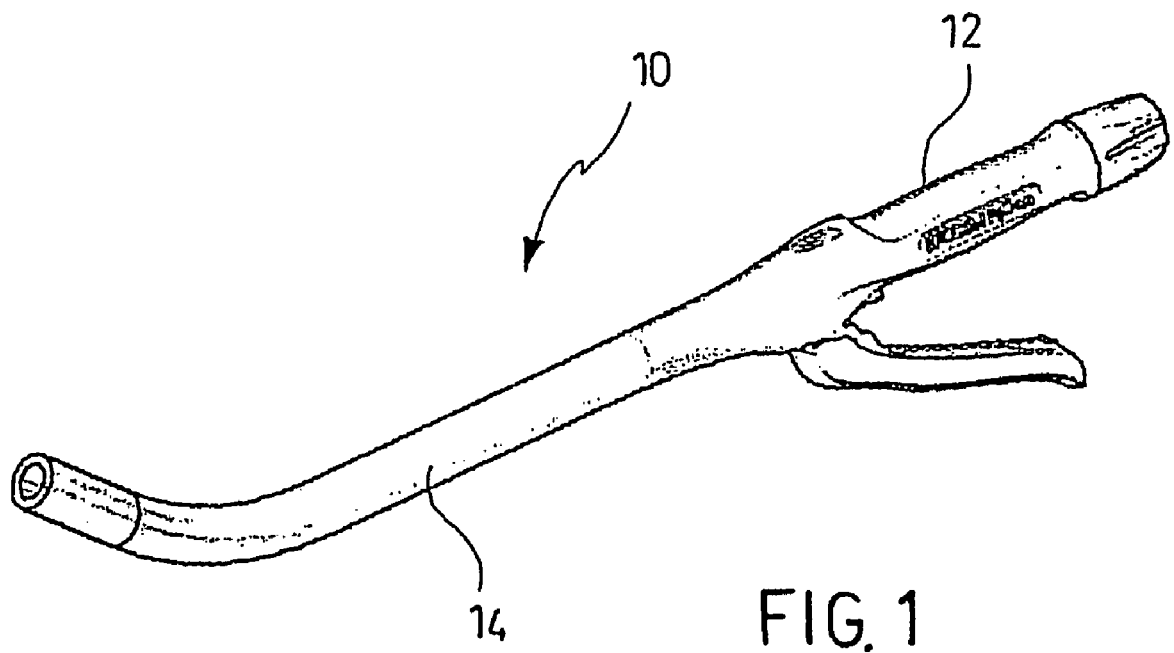
FIG. 1 illustrates a perspective view of a circular stapler.

With reference to FIG. 1, with 10 has been indicated a circular stapler portion comprising a handle 12 and a stem 14 as a whole. The structure of the circular stapler is similar to the known circular staplers, which are conventionally used to carry out circular anastomosis, such as of the bowel. The structure of the circular stapler according to the present invention is changed compared with the conventional ones in that, in a preferred embodiment thereof, it has a channel suitable to receive the guide wire. In FIG. 2A, the circular stapler 10 has a channel crossing the stem 14 thereof from the distal end to an area at the proximal end from which it protrudes outside, for example on one side. In accordance with different embodiments, not illustrated, the guide wire runs all along the length of the circular stapler or only a distal portion thereof.

The channel is suitable to receive a guide wire (not illustrated in FIG. 1) such that the stapler can slide therealong and be placed in the site requiring anastomosis. An exemplary use of the circular stapler 10 will be described below with particular reference to FIG. 29. The length of the stem 14 and the diameter thereof are sufficient to carry out the method and reach the desired site.

Advantageously, the stem is made of a flexible material, such as to facilitate reaching the site requiring anastomosis.

Figure 2:
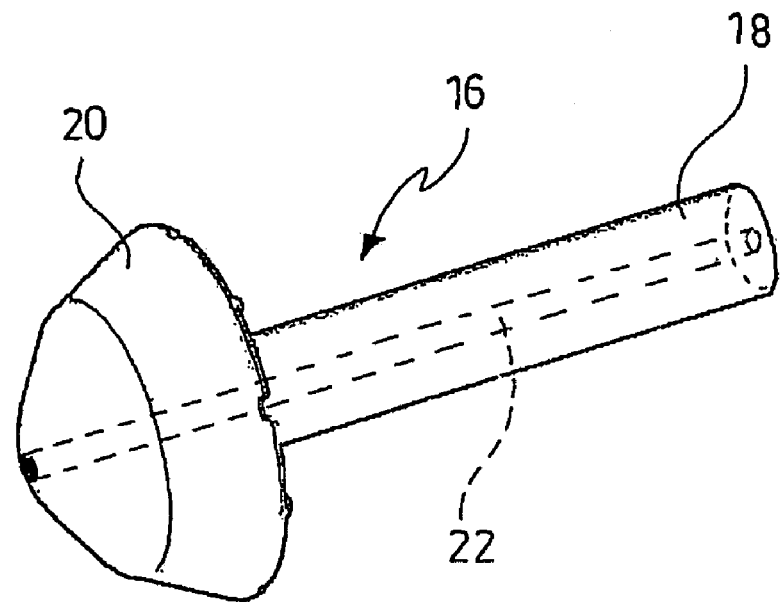
FIG. 2 illustrates a perspective view of a device to be associated with the circular stapler from FIG. 1.

The stapler 10 advantageously comprises an anvil 16 illustrated for example in FIG. 2. The anvil 16 defines an exemplary device for drawing tissues together, particularly a device that, besides drawing the tissues together, is suitable to be associated with the circular anvil 10 such as illustrated in FIG. 1 in order to carry out anastomosis.

The anvil 16 comprises a stem 18 and a head 20. The stem 18 has such a longitudinal and cross size that makes it suitable to be fit on the end of the stem 14 of the circular stapler 10 opposite the handle 12 (FIGS. 2A and 41-44).

Advantageously, a channel 22 crosses the anvil 16 in a longitudinal direction and is suitable to receive a guide wire, not illustrated in FIG. 2. An exemplary use of the anvil 16 for the circular stapler 10 will be described below with particular reference to FIG. 26-29. An anchoring ring suitable to lock the anvil 16 on the guide wire on which it is fitted such as to be drawn by the guide wire in order to draw the tissues together and create the anastomosis has been designated with 76.

Figure 3:
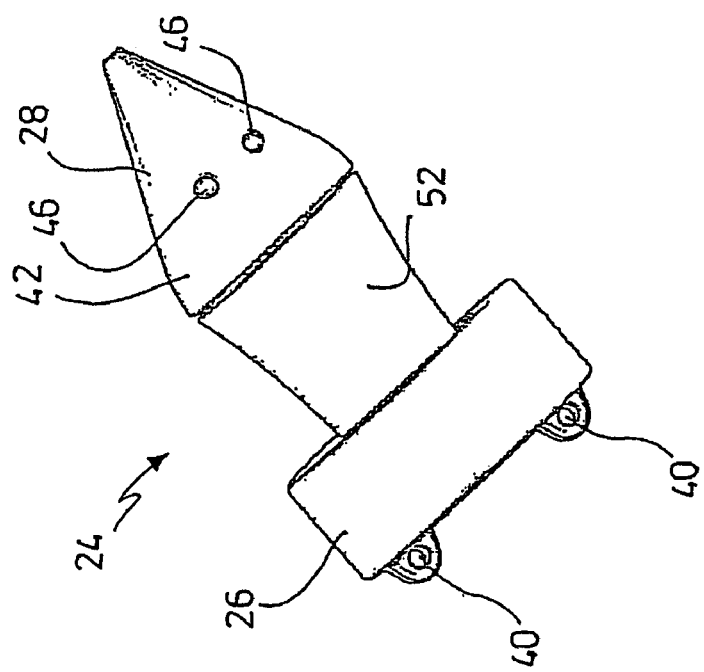
FIG. 3 illustrates a perspective view of a possible embodiment of a positioning device.

In FIG. 3, with 24 has been generally designated a positioning device suitable to draw tissues together which have been subjected to enterostomy, and to place means for providing a passage (anastomosis) between the tissues that have been drawn together.

Figure 8:
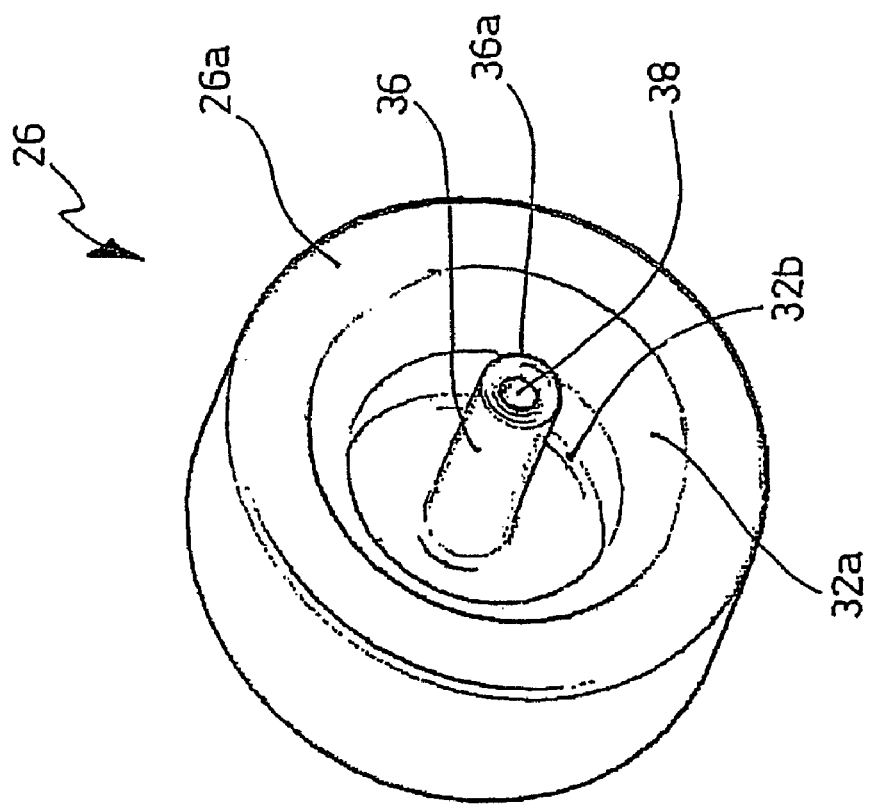
FIGS. 7 and 8 illustrate perspective views of the detail from FIG. 5 from different points of view.
Figure 7:
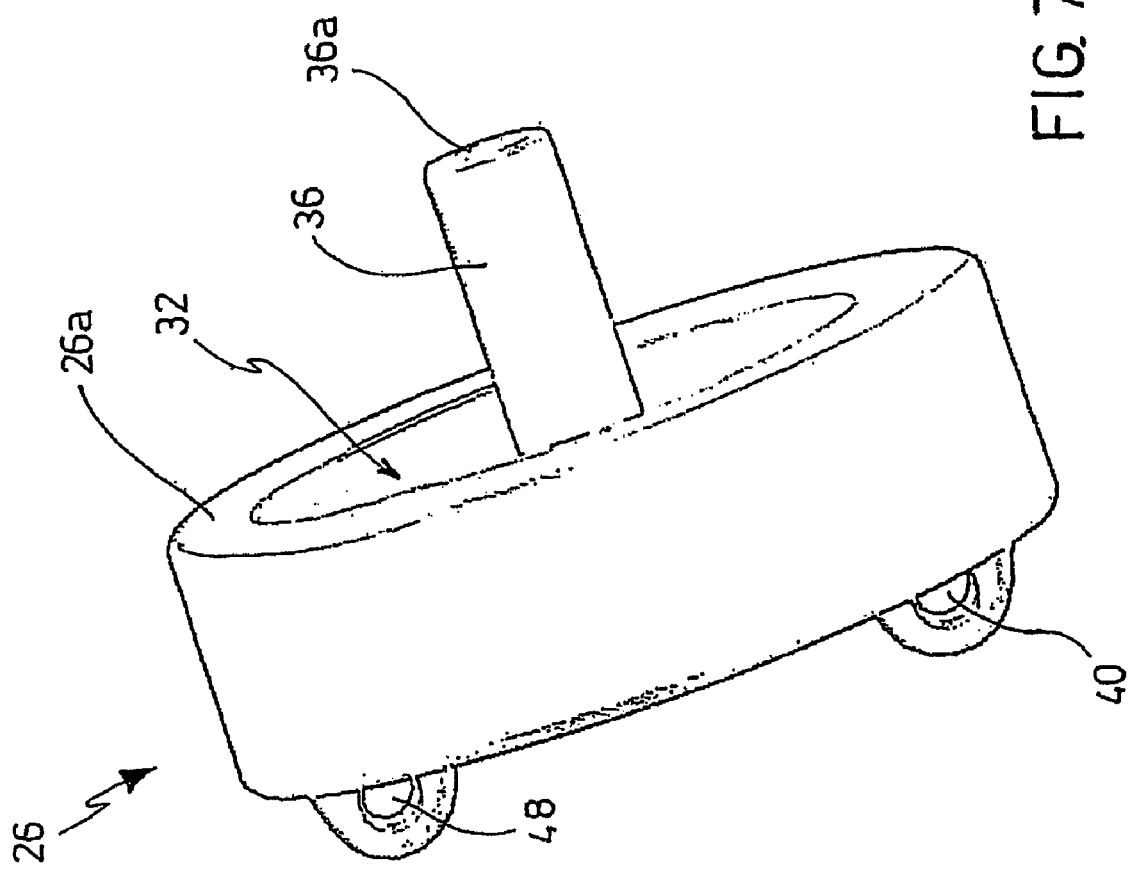

The positioning device 24 comprises a first component, or proximal component, designated with numeral 26 and a second component, or distal component, designated with reference 28. Preferably, the positioning device 24 extends along a longitudinal axis 30. FIGS. 5, 7 and 8 illustrate perspective views of the proximal component 26, whereas FIG. 6 illustrates a perspective view of the distal component 28.

In accordance with a possible embodiment, the proximal component 26 is suitably shaped to be abutted against the edge of a first enterostomy in order to draw the tissues adjacent thereto against the tissues adjacent to a second enterostomy. The distal component 28 is suitably shaped to be inserted through the enterostomies.

For clarity purpose, the first enterostomy will be also called herein below as the proximal enterostomy, whereas the second enterostomy will be also called the distal enterostomy. With reference to a possible embodiment, the first enterostomy can be a gastrostomy and the second enterostomy can be a jejunostomy. With reference to a different embodiment, the first enterostomy can be a proximal jejunostomy and the second enterostomy can be a distal jejunostomy.

In accordance with a possible embodiment, the proximal component 26 has a substantially cylindrical outer structure. A cavity 32 being formed at one of the bases of the cylindrical structure and longitudinally thereto, preferably has a first portion defined by a surface having the shape of a truncated cone 32a and a second portion defined by a cylindrical surface 32b. The cavity 32 does not run through the entire length of the proximal component 26, leaving a base wall 34. Furthermore, the cross size of the cavity 32 and the proximal component 26 are preferably such as to leave an abutment surface, for example a plane annular surface 26a contouring the cavity.

According to a possible embodiment, a lug 36, preferably cylinder shaped, extends along the longitudinal axis 30 from the bottom of the cavity 32 towards the outside of the cavity, preferably such that a free end 36a of the lug 36 is completely out of the cavity 32. In other words, the length of the lug 36 from the base of cavity 32 to the free end 36a thereof is preferably greater than the depth of the cavity 32. The lug 36 has a preferably cylindrical cavity 38 extending along the longitudinal axis 30 and crossing the base wall 34 leading to the opposite surface of the proximal component 26. In other words, the cavity 38 involves the lug 36 and base wall 34 thereby generating a duct open at the ends thereof and suitable to receive a guide wire not illustrated in FIG. 3-8. Preferably, the proximal component 26 comprising the lug 36 is made as one piece.

According to a possible embodiment, the proximal component 26 comprises holes 40 for example for a suture, which can be used for separating the proximal component from the distal component, to be passed therethrough.

In accordance with a possible embodiment, the distal component 28 comprises a head 42 and a stem 44, which are preferably made as one piece, that develop along the longitudinal axis 30.

The head 42 preferably has a shape of a truncated cone and, according to a possible embodiment, comprises holes 46 for a suture, which can be used for example to separate the distal component from the proximal component, to be passed therethrough.

In accordance with a possible embodiment, the stem 44 preferably has a cylindrical structure and a free end thereof, i.e. opposite the head 42, widens to form a preferably annular base 48.

Figure 4:
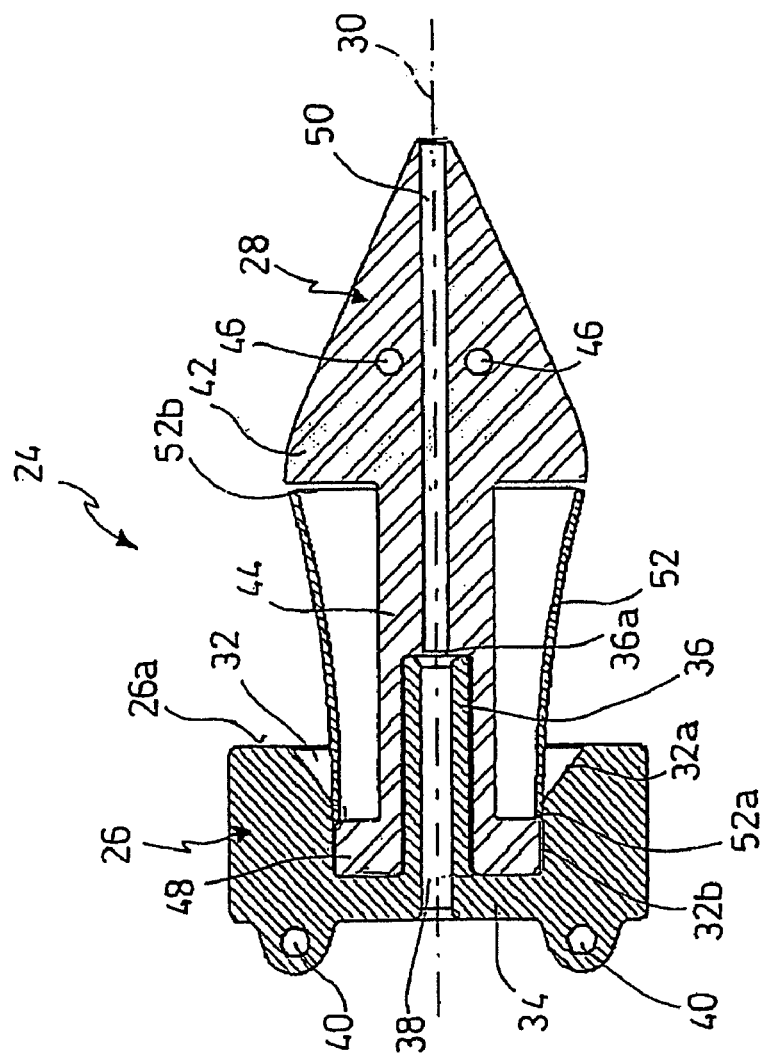
FIG. 4 illustrates a sectional view along a plane containing a longitudinal axis of the device from FIG. 3.

A channel 50 extends along the longitudinal axis 30 from the end of head 42 to the base 48 and is suitable to receive a guide wire therein, not illustrated in FIG. 4 or 6. The cross size of channel 50, at least in the portion at the base 48, are such as to receive the lug 36 of the proximal component 26 therein. In other words, the channel 50 preferably has a larger section at the area in which it receives the lug 36. Preferably, the remaining part of channel 50 has the same cross size as the cavity 38.

FIGS. 3 and 4 illustrate the positioning device 24 when assembled. The proximal component 26 and the distal component 28 are joined such that the cavity 38 and channel 50 define a channel running all along the assembly for introducing a guide wire, not illustrated in FIGS. 3 and 4. Particularly, FIG. 4 illustrates the positioning device 24 sectioned along a plane comprising the longitudinal axis 30. In the assembly position, the proximal component 26 and the distal component 28 lock an elastic ring 52 therebetween, which is hold in a compressed/deformed configuration, and suitable to be placed by the positioning device 24 in a desired anastomotic site in which, after it has been positioned, the elastic ring 52 takes a preset non-compressed rest shape (see for example FIG. 37). The elastic ring can be made of Nitinol, stainless steel or other satisfying materials.

In accordance with a possible embodiment, the elastic ring 52 in its deformed configuration, has an end, such as the proximal (designated with numeral 52a), that is locked between the base 48 of the distal component 28 and the inner diameter of the cavity 32 of the proximal component 26, i.e. inside the cylindrical portion 32b of the cavity 32. The opposite end of the elastic ring 52, i.e. the distal end designated with the numeral 52b, is preferably unfastened and abuts beneath the head 42 of the distal component 28. In this case, it is advantageously provided that the cross size of the distal end 52b of the elastic ring 52 does not exceed the cross size of the head 42 of the distal component 28.

An exemplary use of the positioning device 24 will be described below with particular reference to the FIG. 34-37. Upon use, the outer diameter of the proximal component, and particularly with the flat annular surface 26a, is intended to act as a striker against the wall of the tissue to be drawn together, or in other words, abut against the proximal enterostomy while it minimizes the risk of penetration in the wall.

The distal component 28, with its head 42, is intended to penetrate in the proximal and distal enterostomies and protects the elastic ring 52 while being inserted and positioned, such as will be described in the following.

FIG. 9-12 illustrate a possible variant embodiment of the positioning device 24 and the proximal and distal components thereof according to the present invention. The elements in common have been designated with the same numeral used in FIG. 3-8 and will be described below with reference to the differences from the above embodiment.

The proximal component 26 is substantially similar to the one illustrated in FIGS. 3-5, 7 and 8. As regards the distal component 28, the stem 44 extends straight up to its free end opposite the head 42 that does not widen to form a base similar to the base 48 of the distal component described above. Furthermore, the head 42, preferably having the shape of a cone or truncated cone, comprises a flange 54 extending from the outer perimeter of the major base of the head to form a circular wall substantially parallel to the longitudinal axis 30.

Figures 9, 10:
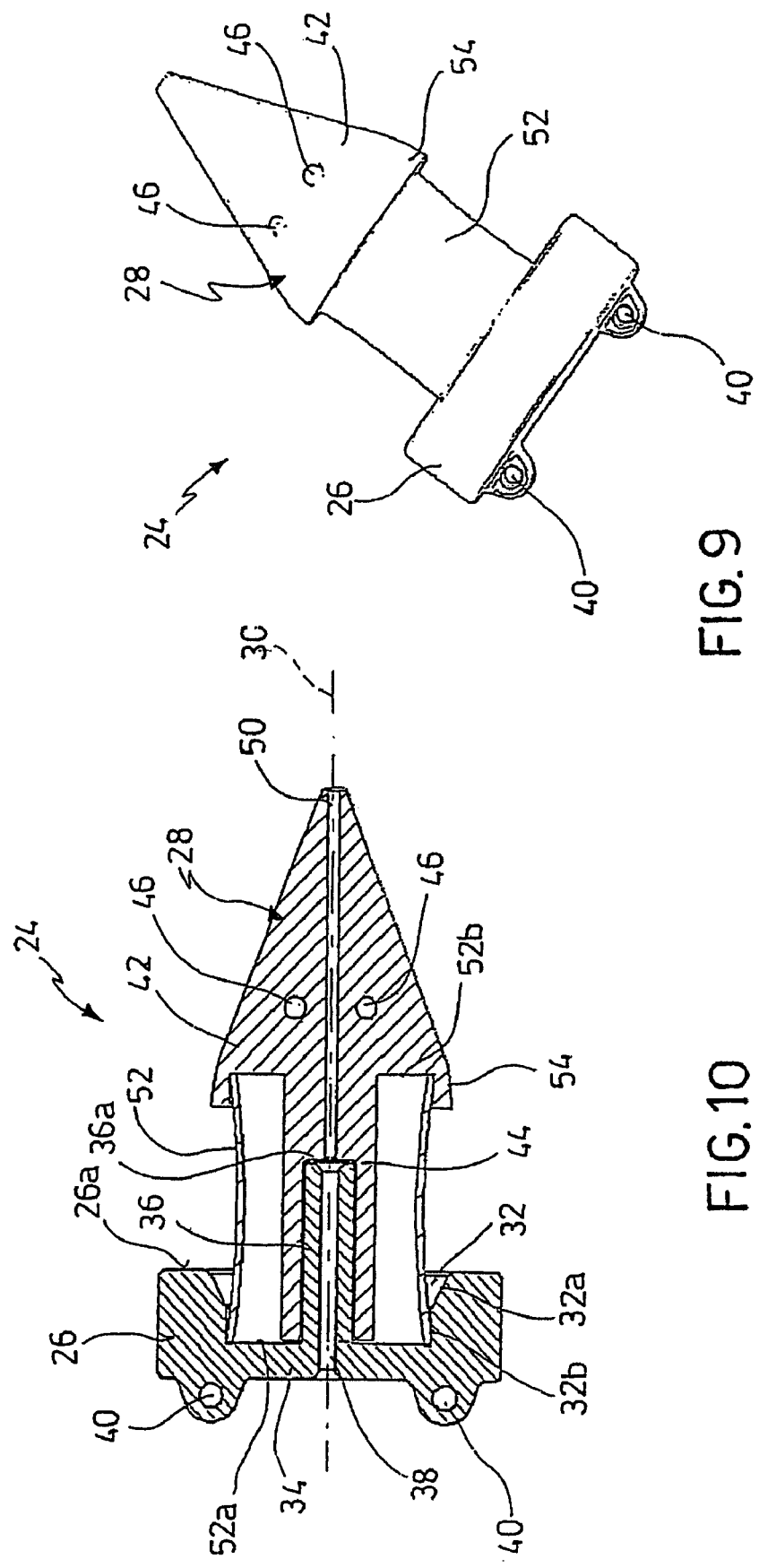
FIG. 9 illustrates a perspective view of a possible embodiment of a positioning device.
FIG. 10 illustrates a sectional view along a plane containing a longitudinal axis of the device from FIG. 9.
Figure 12:
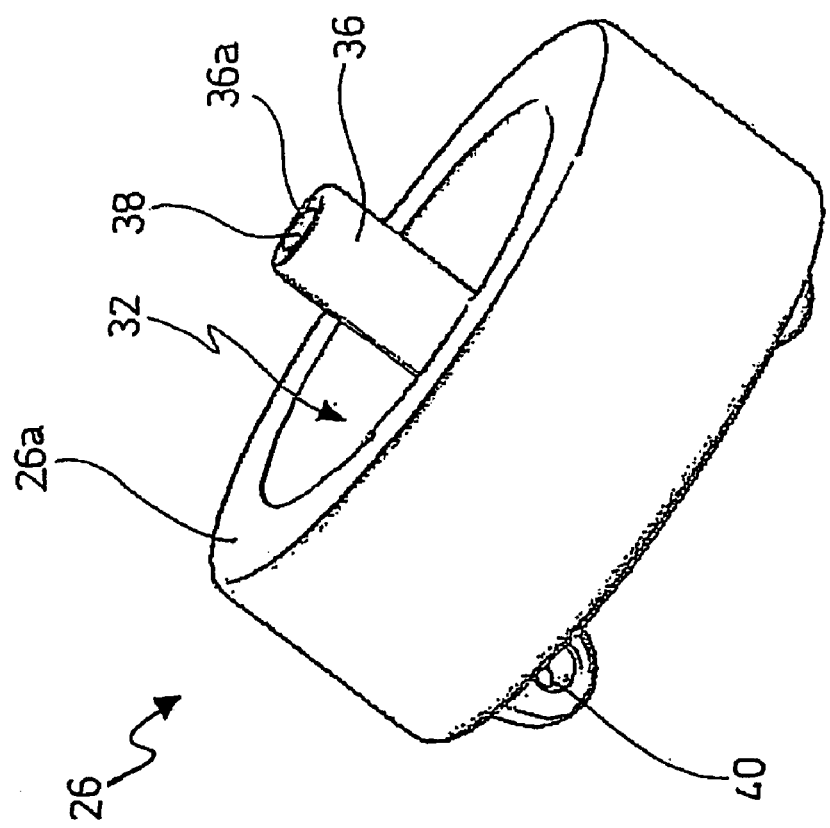
FIG. 12 illustrates a perspective view of a detail of the device from FIG. 9.
Figure 11:
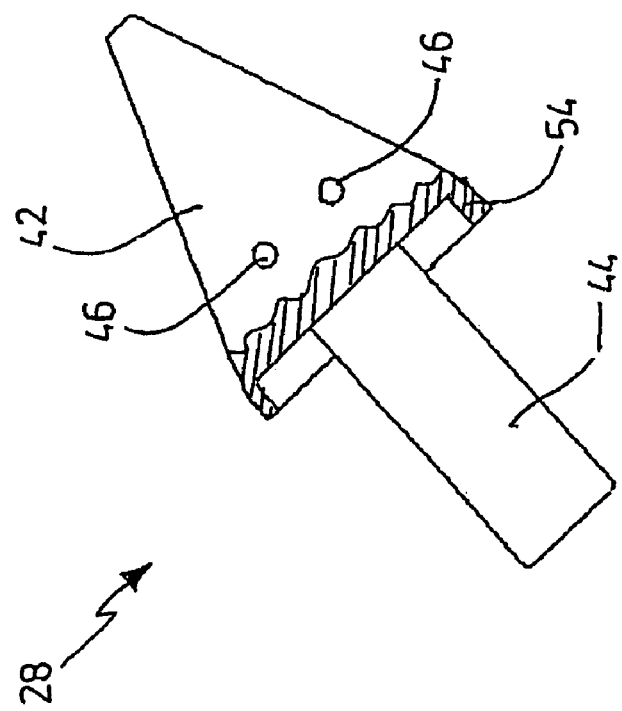
FIG. 11 illustrates a partially sectioned, perspective view of a detail of the device from FIG. 9.

FIGS. 9 and 10 illustrate the positioning device 24 when assembled, in which the channel 50 and the cavity 38 define a channel extending along the longitudinal axis 30 through the entire length of the assembled positioning device 24 to receive a guide wire, not illustrated in the FIG. 9-12. In the assembled configuration of the positioning device 24, the elastic ring 52 is hold between the proximal component 26 and the distal component 28 in a compressed/deformed configuration. After the elastic ring has been positioned, it takes a preset, uncompressed rest shape as described above. In the deformed configuration, the proximal end 52a of the elastic ring 52 is fastened by the inner diameter of the cavity 32, particularly by the cylindrical portion 32b of the cavity 32, whereas the distal end 52b of the elastic ring 52 is fastened within the circular flange 54 of the distal component 28.

The cross size of channel 50, at least in the portion at the base 48, are such as to receive the lug 36 of the proximal component 26 therein. In other words, the channel 50 has a larger section at the area where it receives the lug 36. Preferably, the remaining part of channel 50 has the same cross size as the cavity 38. Also in this case, the elastic ring 52 can be made of Nitinol (Ni—Ti alloy), stainless steel or other satisfying materials.

The exemplary use of the positioning device is similar throughout the various embodiments described.

FIG. 13-16 illustrate a possible variant embodiment of the positioning device and the proximal and distal components thereof according to the present invention. The elements in common have been designated with the same numeral used in the figures above and will be described below with reference to the differences from the above embodiments.

The proximal component 26 has a prismatic outer structure, preferably having a rectangular base. The cavity 32 is formed at one of the bases of the structure and does not run through the entire length of the proximal component 26, leaving a base wall 34. The sizes of the cavity 32 and proximal component 26 are such as to leave a peripheral flat surface 26a.

In the base wall 34, preferably in the middle thereof, there is provided a preferably cylindrical cavity 38 extending along the longitudinal axis 30 and crossing the entire thickness of the base wall.

Ribs 56, preferably on opposite parts of cavity 38 and parallel to the long sides of the rectangular base, extend from the bottom of the cavity 32 by a height preferably less than the depth of cavity 32.

According to a possible embodiment, the proximal component 26 comprises holes 40 for example for a suture, which can be used for separating the proximal component from the distal component, to be passed therethrough.

The distal component 28 comprises a head 42, which according to a possible embodiment, comprises holes (not illustrated) for a suture, which can be used for example to separate the distal component from the proximal component, to be passed therethrough.

Figure 15:
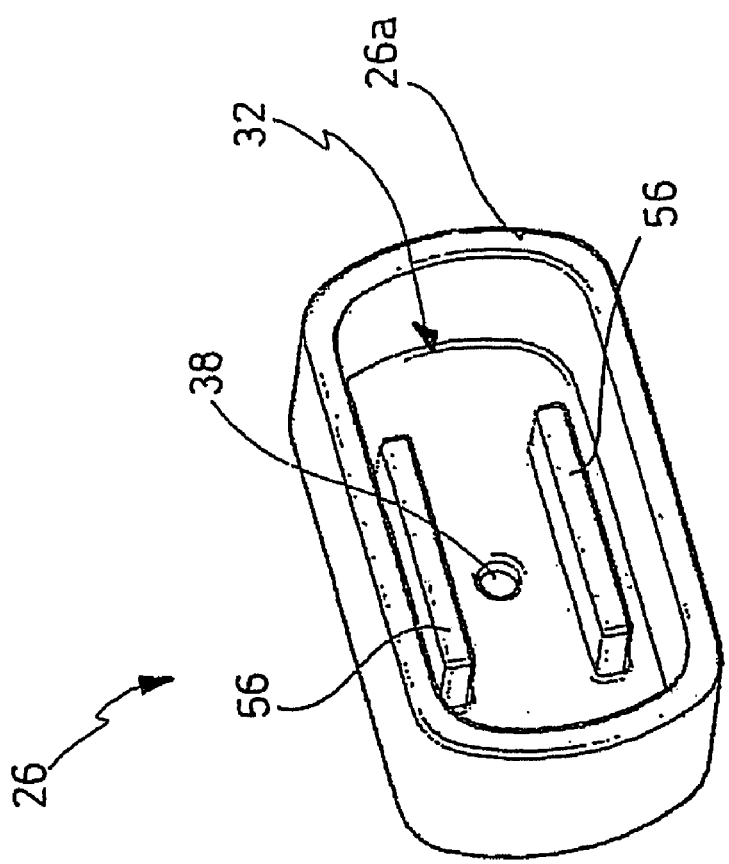
FIG. 15 illustrates a perspective view of a detail of the device from FIG. 13.
Figure 16:
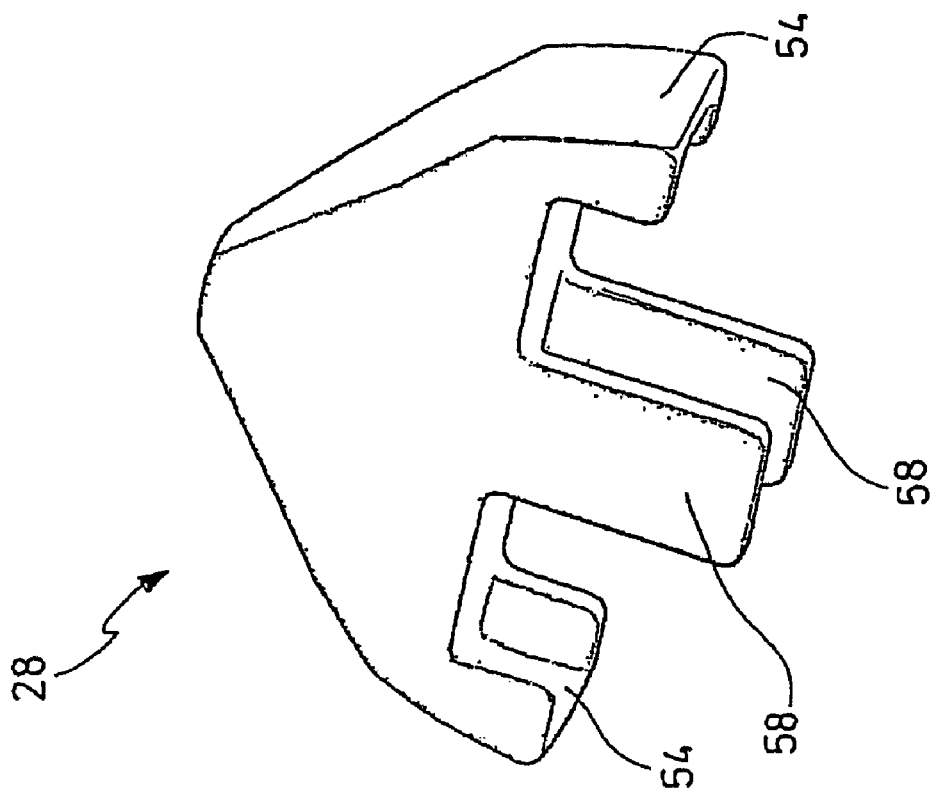
FIG. 16 illustrates a perspective view of a detail of the device from FIG. 13.

The channel 50 extends along the longitudinal axis 30 throughout the solid thickness of the head 42, preferably in the middle thereof, and is suitable to receive a guide wire therein, not illustrated in FIG. 14 or 15.

The head 42 has a tract having a substantially pyramidal or having a truncated-pyramid shape, preferably with a rectangular base. Two flanges 54 that preferably involve the short sides of the rectangular base and a limited portion of the long sides extend from the outer periphery of the major base of the truncated-pyramidal portion, in a direction substantially parallel to the longitudinal axis 30.

According to a possible embodiment, there is provided a preferably flat extension 58, arranged at a middle portion of each long side of the rectangular base and projecting in the direction substantially parallel to the longitudinal axis 30 along a preferably longer tract than the flanges 54.

FIGS. 13 and 14 illustrate the positioning device 24 when assembled, in which the channel 50 and the cavity 38 are arranged along the longitudinal axis 30 to receive a guide wire, not illustrated in the FIG. 13-16. In the assembled configuration of the positioning device 24, the elastic ring 52 is hold between the proximal component 26 and the distal component 28 in a preferably flattened, compressed/deformed configuration. After the elastic ring has been positioned, it takes a preset, uncompressed rest shape as described above. In the deformed configuration, the proximal end 52a of the elastic ring 52 is fastened by the inner periphery of the cavity 32. Particularly, the ribs 56 fasten the elastic ring 52 in a flat deformed configuration, or in other words, the elastic ring 52 is arranged between the wall of the cavity 32 and the ribs 56. Furthermore, the distal end 52b of the elastic ring 52 is fastened by the flanges 54 and extensions 58, when the latter are provided.

On the one hand, the assembled configuration of the positioning device 24 is ensured by the interference between the proximal end 52a of the elastic ring 52 and the walls of the proximal component 26 defining the cavity 32, and on the other hand by the interference between the distal end 52b of the elastic ring 52 and the flanges 54 and the extensions 58, when the latter are provided.

Also in this case, the elastic ring 52 can be made of Nitinol, stainless steel or other satisfying materials.

The exemplary use of the positioning device is similar throughout the various embodiments described. In this latter case, the peripheral wall 26a of the proximal component 26 is the one intended to abut against the wall of the tissue to be drawn together while minimizing the risk that the wall may be penetrated. Furthermore, the angled head 42 of the distal component 28 is intended to penetrate the proximal and distal enterostomies and protects the elastic ring 52 when being introduced and positioned by fastening the ring within the flanges 54 and the extensions 58, such as will be described in the following.

The channel 50 and the cavity 38 are intended to house a guide wire for transporting the positioning device.

The present invention further relates to a method for the therapy of obesity and particularly a method for carrying out anastomosis in tracts of the digestive tube. FIG. 17-40 illustrate several steps of a possible embodiment of the method according to the present invention. The examples illustrated particularly relate to a method for carrying out an endoluminal/transluminal gastrojejunostomy (G-J) and a jejunojejunostomy (J-J) via transoral access.

In general terms, the method according to the present invention advantageously provides to draw tissues together and carry out anastomosis via endoluminal access by introducing, through a natural orifice (such as nose, mouth, ears, anus) or other luminal structures, guide or rail means within the tissues to be drawn together. Suitable components or devices can be thereby carried to the anastomotic site such that the surfaces of the tissues are suitably drawn together and connected with a channel (anastomosis).

Advantageously, the guide or rail means, particularly a main guide wire or first guide wire, are introduced such as to generate an open ring that can begin and end in natural orifices, such as the mouth, nose, anus or other natural orifices, such as colostomy, trocar, abdomen incisions, wounds, fistulae. The components or devices provided to draw the tissues together are advantageously moved by locking the device on the guide wire and pulling one of the guide wire ends.

In accordance with a possible embodiment, the ends of the open ring and accordingly of the main guide wire are different from each other, and hence distinguishable. Advantageously, the guide wire is internally hollow, i.e. it has a tubular structure suitable to receive needles for perforating the tissues and carrying out proximal and distal enterostomies. Perforation can take place for example either by pushing the needle through the tissues, or applying a radiofrequency through the needle.

The open ring then crosses the proximal enterostomy and then the distal enterostomy, for example by using a gripping device.

The positioning device 24 is locked on the guide wire by means of an anchoring ring 76 and drawn by the guide wire until it is partially inserted in the proximal enterostomy and abutted against a first tissue portion to be joined. The positioning device 24 is further drawn until it is partially inserted in a distal enterostomy by drawing together the tissue portions to be joined. Finally, the positioning device 24 partially inserted in the proximal and distal enterostomy releases an elastic ring 52 riding the proximal and distal enterostomies to hold the tissue portions joined to each other thereby generating a passage or anastomosis.

With reference to the above example, FIG. 17-29 illustrate a gastrojejunostomy (G-J) step that is advantageously carried out by introducing guide or rail means through a natural orifice (such as the nose or mouth). Subsequently, the guide means, a guide wire in this case, form an open ring crossing the points of the tissues to be joined.

Figure 17:
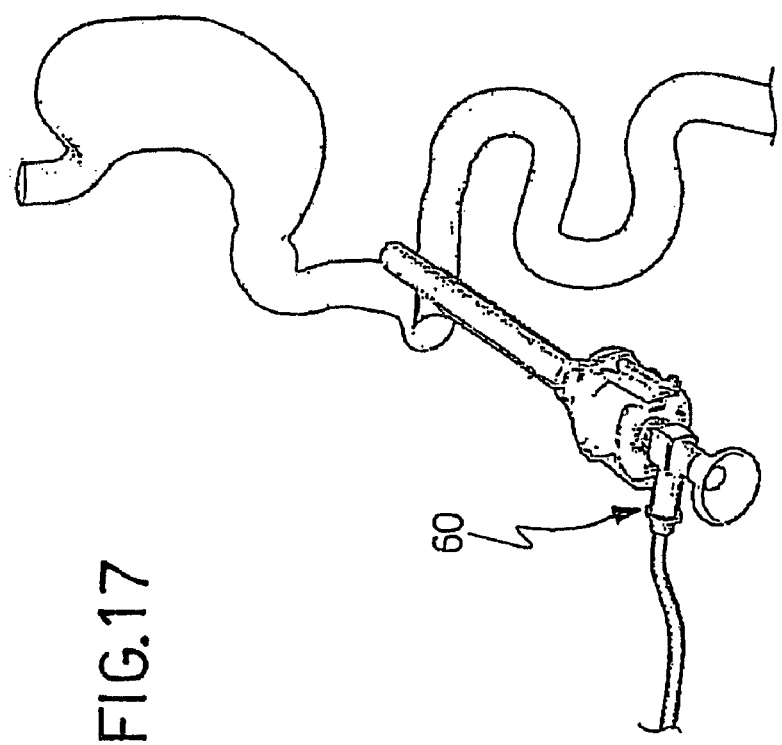

FIG. 17 illustrates a first step, which is designated as the step 1, in which a substantially conventional laparoscope 60 has been introduced in the abdominal cavity to view the areas to be treated. This step can be potentially eliminated after a certain degree of skill in the method has been achieved, thereby the method can be made completely endoluminal and transluminal. The laparoscope 60 is illustrated in FIG. 17 and also in the subsequent steps, but it can be omitted as well. Alternatively or in addition to the laparoscopic control, a gastroscopic control can be provided, i.e. by introducing a secondary gastroscope for example through the esophagus or mouth having the function of controlling the method steps. In case a gastroscope is required to carry out several steps of the method, a main gastroscope carrying out the method steps and a secondary gastroscope monitoring the operation will be introduced.

Figure 18:
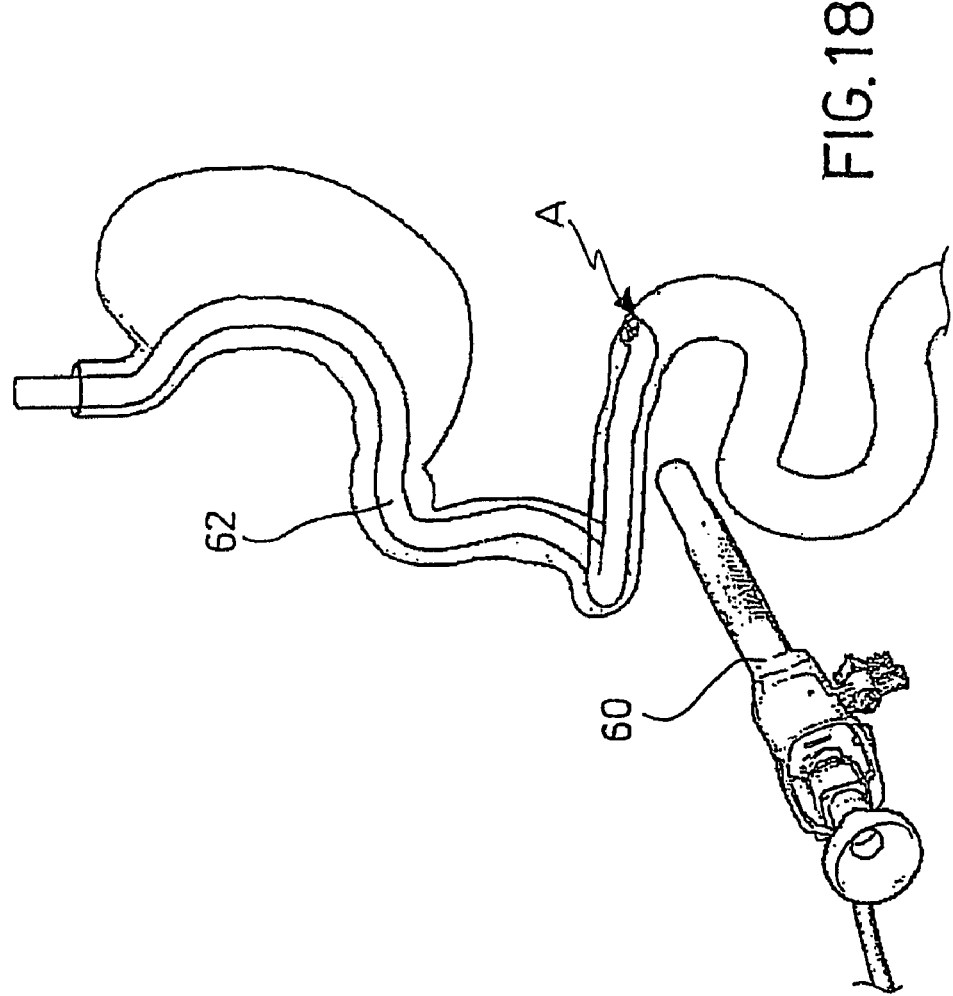

FIG. 18 illustrates a step of the method according to the present invention, which is also designated as the step 2, in which a substantially conventional main gastroscope 62 is introduced through the esophagus, stomach, passing through the pylorus and subsequently the duodenum to reach the jejunum. Particularly, the gastroscope 62 is advanced by approximatively 20-40 cm beyond the pylorus.

Figure 19:
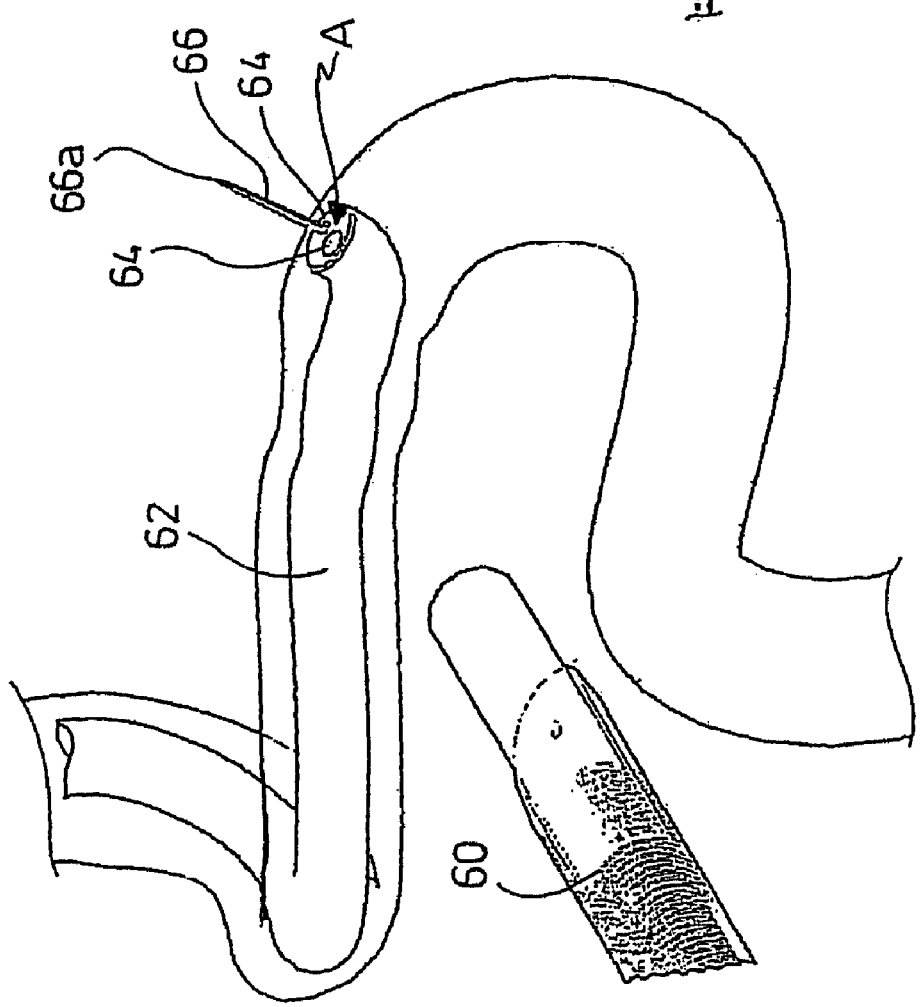

FIG. 19 illustrates a detail of the jejunum and the end of the gastroscope 62. The latter conventionally comprises several channels 64 crossing the entire length thereof and that can be used for tools or the like to be passed therethrough. The step from FIG. 19, also designated as the step 3, provides that a first guide wire 66 or main guide wire being suitable to provide the open ring is advanced along one of the channels 64 of the gastroscope 62. The guide wire is advanced until a pointed end 66a thereof or a needle sliding along the tubular structure of the guide wire protrudes from the gastroscope. The end 66a of the guide wire 66 perforates the jejunum wall from the inside and creates a jejunostomy (proximal enterostomy). The laparoscope 60 is optionally provided. When this is provided, the guide wire 66 is advanced and the jejunostomy is created under the laparoscope visual control.

The jejunostomy can be carried out by pushing the guide wire directly through the jejunum wall. Alternatively, or in addition thereto, radiofrequency energy may be applied to perforate the jejunum wall and then advance the guide wire 66.

In other words, a first guide wire 66 being part of guide or rail means which will be subsequently indicated in greater detail, is positioned within the tissue to be joined and passed through one of the tissue portions to be joined. The jejunum tissue portion to be drawn near and joined to the stomach thereby forming an anastomosis has been designated with A.

Figure 20:
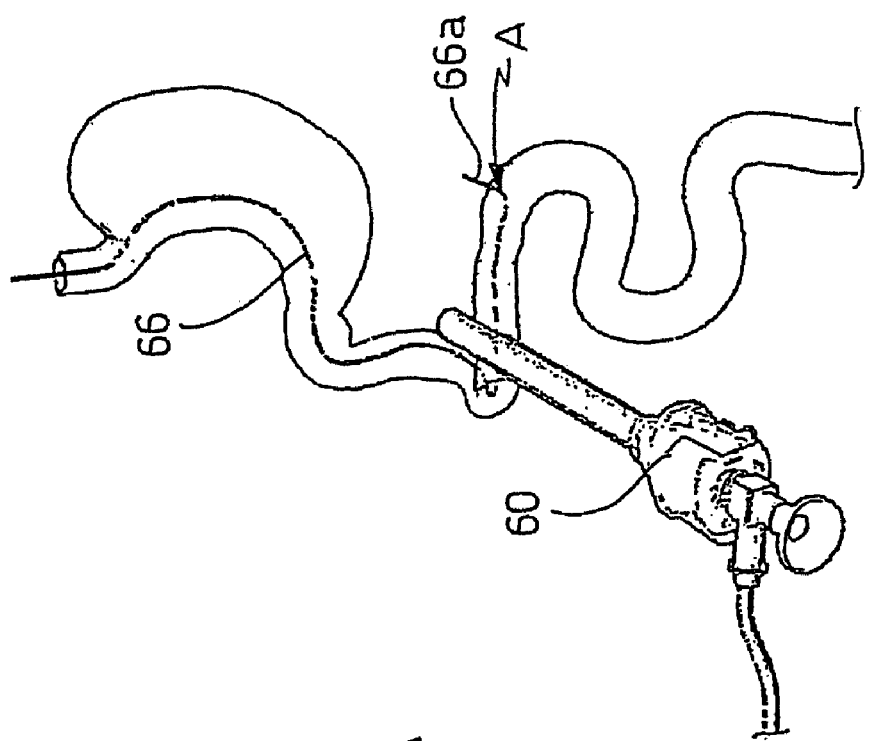

FIG. 20 illustrates a step which has been designated as the step 4 in which the gastroscope 62 is removed and the guide wire 66 is left in the abdomen within the stomach and along a jejunum tract with the end 66a protruding from the jejunum at the tissue portion A to be joined. The step 4 can be carried out under laparoscopic control (laparoscope 60), when provided.

Figure 21:
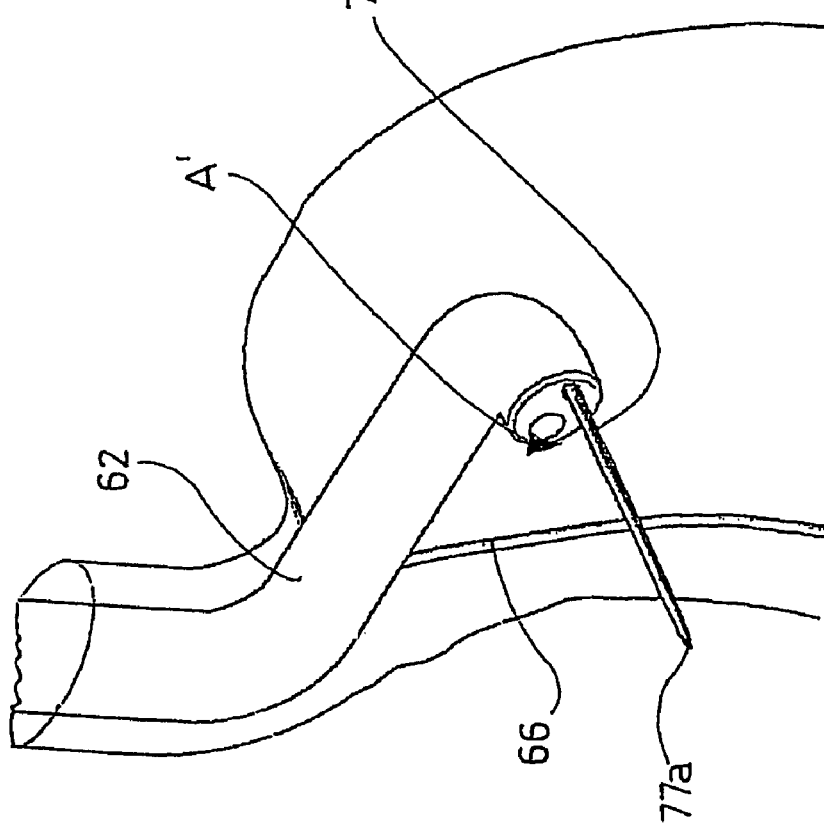

FIG. 21 illustrates a step which is designated as the step 5, in which a main gastroscope 62, of a substantially conventional type, has been introduced again in the stomach through the esophagus, in order to create a gastrostomy (distal enterostomy). Also in this case, one may directly push either a secondary guide wire 77 with a pointed end 77a or a needle sliding within the tubular structure of the guide wire. Alternatively, or in addition thereto, radiofrequency energy can be applied in order to perforate the stomach wall and advance the guide wire.

The gastrostomy is carried out in a stomach portion corresponding to the area to be joined. This portion has been designated with A'.

Step 5 may also be carried out under laparoscopic control.

Figure 22:
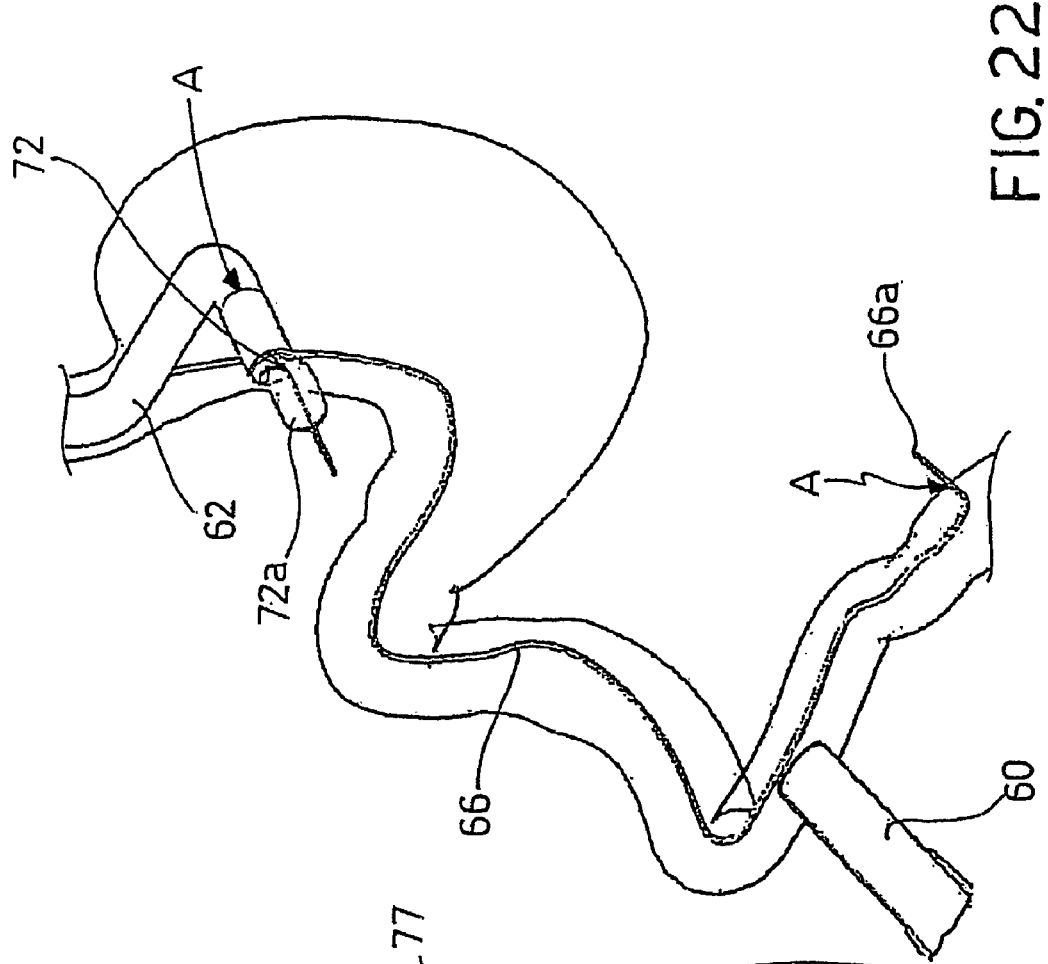

FIG. 22 illustrates a step of the method according to the present invention, which has been designated as the step 6, in which the gastrostomy is enlarged by means of a balloon catheter 72. The catheter is inserted in the gastroscope 62 until a balloon-end 72a thereof reaches the gastrostomy which is enlarged by inflating the balloon.

Step 6 may also be carried out under laparoscopic control.

Figure 23:
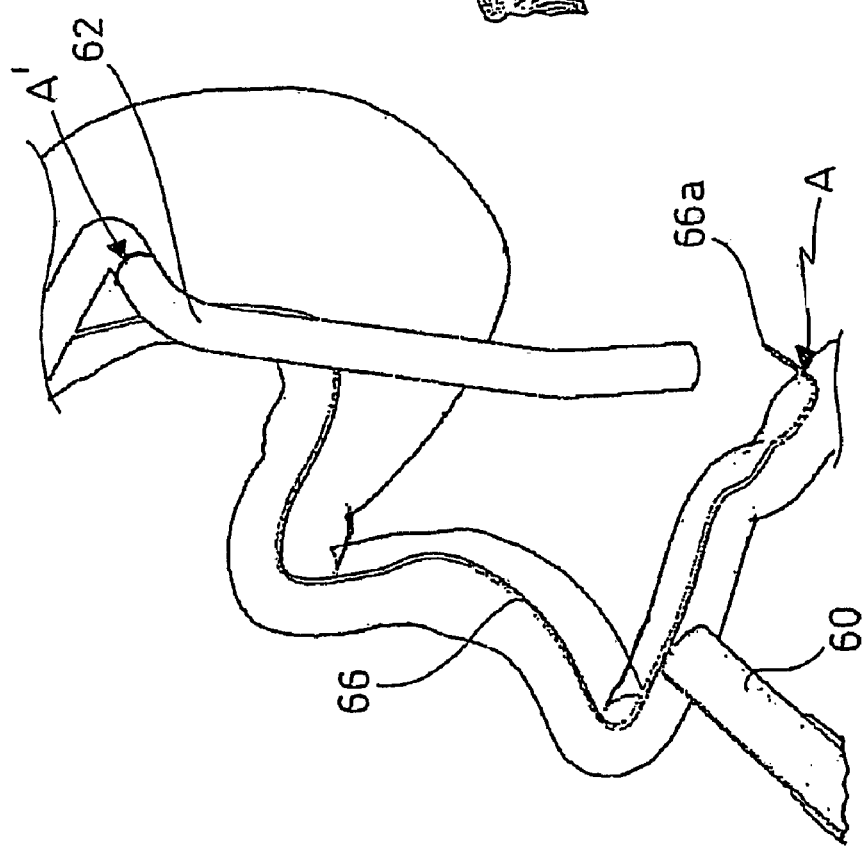

FIG. 23 illustrates a step of the method according to the present invention, which has been also designated as the step 7, in which the gastroscope 62 is advanced through the gastrostomy enlarged by the balloon, within the abdominal cavity. Step 7 can be carried out either under gastroscopic (secondary gastroscope) and/or laparoscopic (laparoscope 60) control. As stated above, by gastroscopic control is meant a control carried out by means of a secondary gastroscope, not illustrated in FIG. 23, which is introduced through the esophagus having only a control function. This secondary gastroscope can be provided in every step whenever a gastroscopic control as an alternative or in addition to the laparoscopic control is required.

Figure 24:
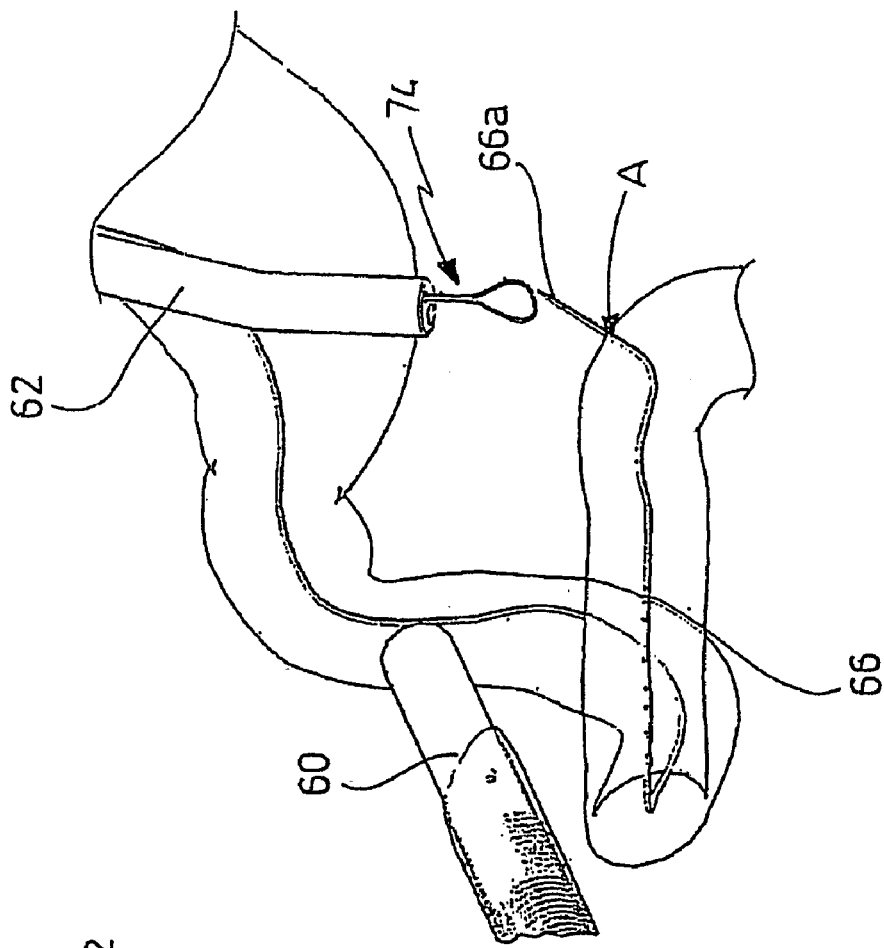

FIG. 24 illustrates a step which has been designated as the step 8, in which a gripping device 74 (forceps or the like) is advanced through the gastroscope 62 and the end 66a of the guide wire 66 protruding from the jejunostomy is coupled therethrough. Gripping the guide wire point is not required.

The gripping device 74 can be for example a loop-shaped endoscopic instrument for polypectomies.

Figure 25:
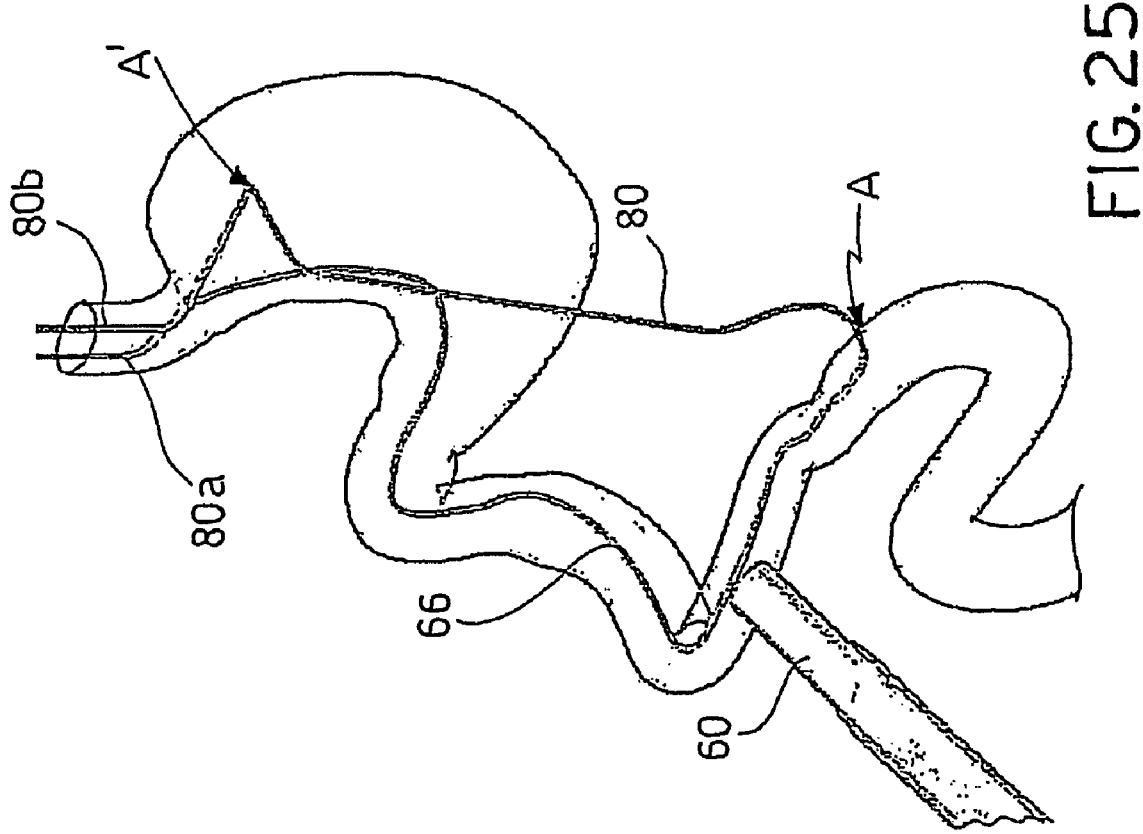

FIG. 25 illustrates a step which has been designated as the step 29, in which the guide wire 66 of the jejunum is pulled through the gastrostomy in order to provide a first ring 80 open at the ends thereof, or gastro-jejunum ring (ring 1), the ends thereof protruding from the orifice used (the mouth, esophagus, . . . ). In FIG. 25, the end of ring 80 corresponding to the jejunum (jejunum end), i.e. the end passing through the stomach and jejunum and protruding from portion A has been designated with 80a, whereas the end of the ring 80 corresponding to the stomach (stomach end), i.e. the end passing through the stomach and protruding therefrom at portion A' has been designated with 80b. Both ends are advantageously different from each other in order to be distinguished.

The ring 80 can be now used as a guide means or rail system in order to introduce and carry suitable anastomotic devices suitable to draw the tissues together and carry out the anastomosis in the site of interest. The anastomotic devices are advantageously locked on the guide wire for example by means of an anchoring ring 76 and one of the ends of the ring is pulled until the anastomotic device partially enters the proximal enterostomy, draws the tissues thereof near the distal enterostomy and partially enters the same.

Figure 26:
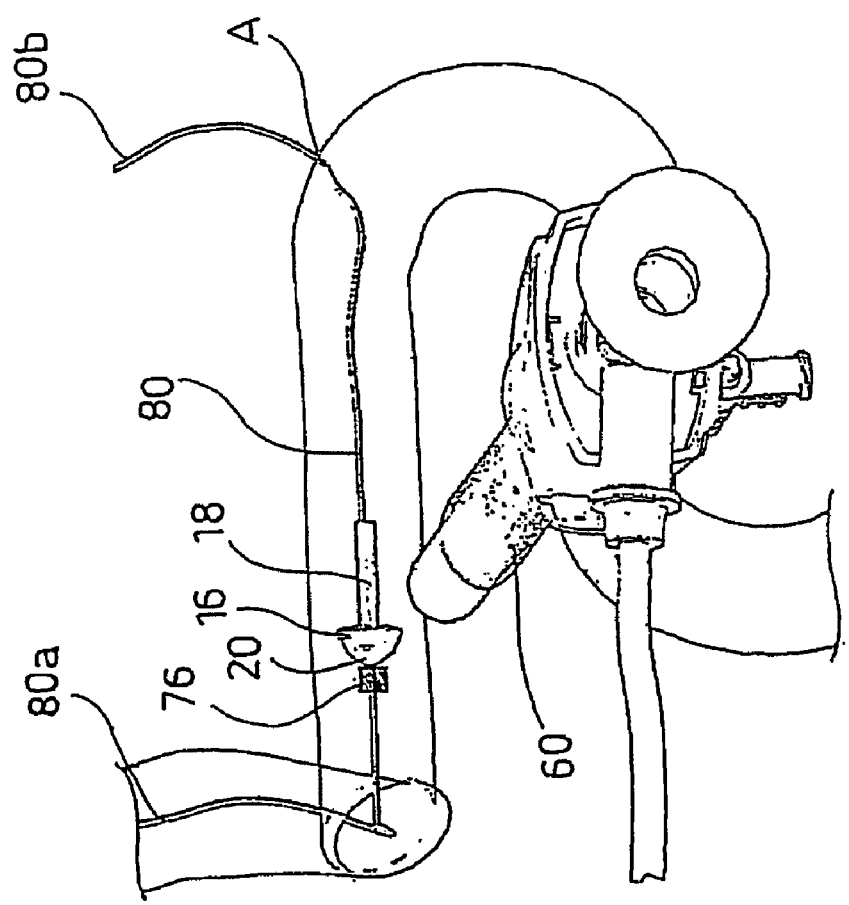

FIG. 26 illustrates a step which has been designated as the step 10, wherein the selected anastomotic device (anvil 16, positioning device 24, etc.) is inserted on the guide wire from the jejunum end 80a and pulled along the ring 80 of guide wire through the esophagus, stomach, duodenum and jejunum. Drawing is allowed by an anchoring ring 76 which is made integral with the guide wire such as to push against the proximal part of the selected anastomotic device.

Though an anvil 16 has been illustrated in FIG. 26, a positioning device 24 or other similar devices can be used as well.

By pulling the guide wire from the end of stomach 80b, the anastomotic device can be pulled until the portion A of the jejunum (proximal enterostomy).

As illustrated in FIG. 26, the end of the jejunum part of the guide wire 80a is inserted in the channel 22 of the anvil 16 from the side of the stem 18. In the case of the positioning device 24, the end of the jejunum part of the guide wire 80a would be inserted in the channel 50 from the side of the distal component 28.

Figures 27, 28:
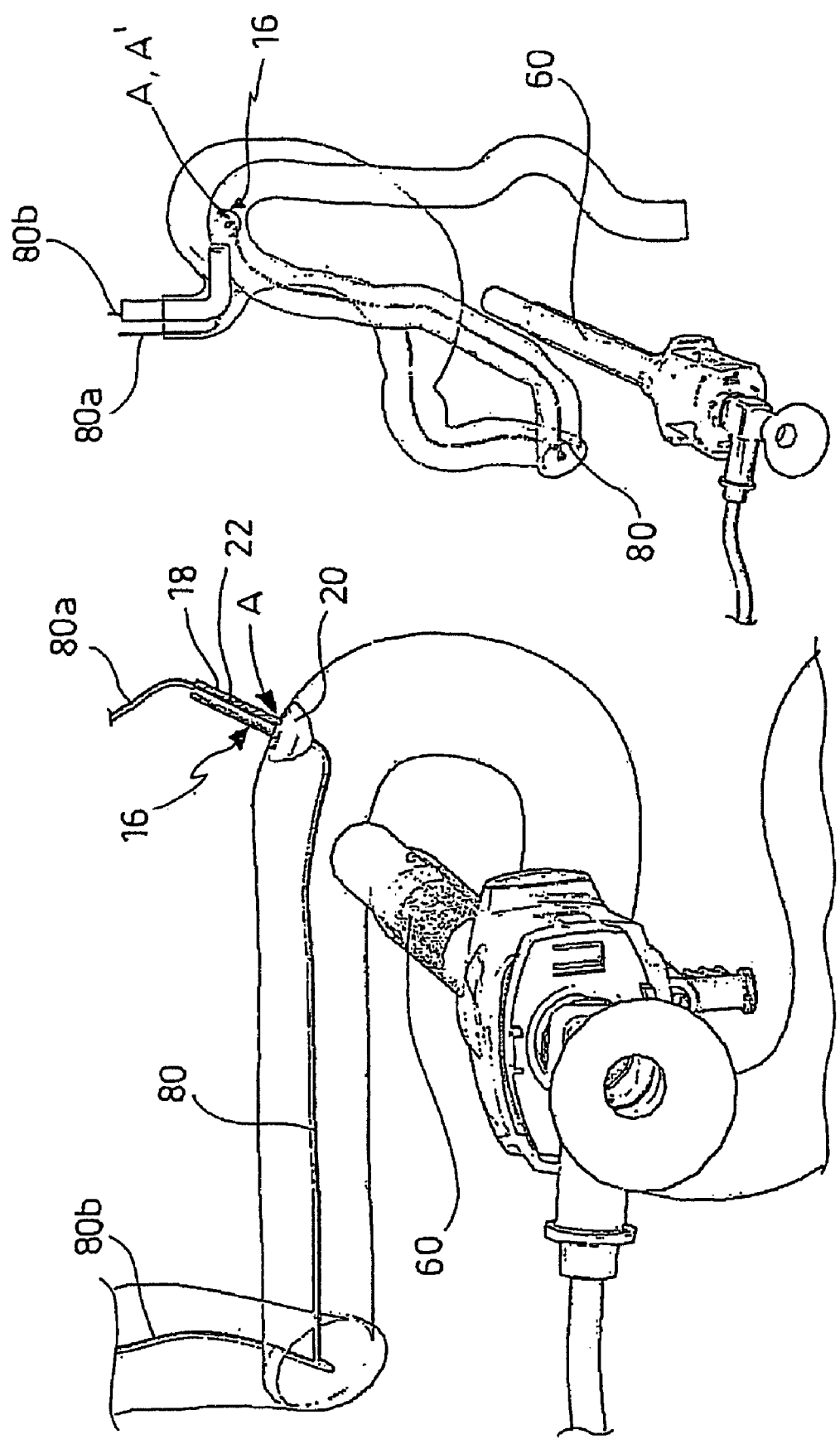

FIG. 27 illustrates a step which has been also designated as the step 11, in which the anastomotic device and particularly the anvil 16 is pulled until it has partially passed the jejunostomy (proximal enterostomy). As already stated above, one can act under laparoscopic control. The stem 18 of the anvil 16 crosses the jejunostomy and protrudes in the abdominal cavity, whereas the head 20 contacts the tissue to be drawn together. When a positioning device 24 is used, the head would enter the jejunostomy whereas the flat peripheral surface 26a would abut against the contouring tissues.

FIG. 28 illustrates a step which has been also designated as the step 12, in which by keeping on pulling the end of the guide wire 80b from the side of the stomach, the anvil 16 and particularly the head 20 acts as a striker against the inner wall of the portion A of the jejunum and draws the jejunum until the portion A is drawn near the stomach and particularly portion A'. The stem 18 of the anvil 16 (anastomotic device) also partially enters the gastrostomy (distal enterostomy). The operation can be carried out under laparoscopic control (laparoscope 60). When a positioning device 24 is used, the head would 42 enter the gastrostomy whereas the flat peripheral surface 26a would draw the relative contouring tissues together.

Figure 29:
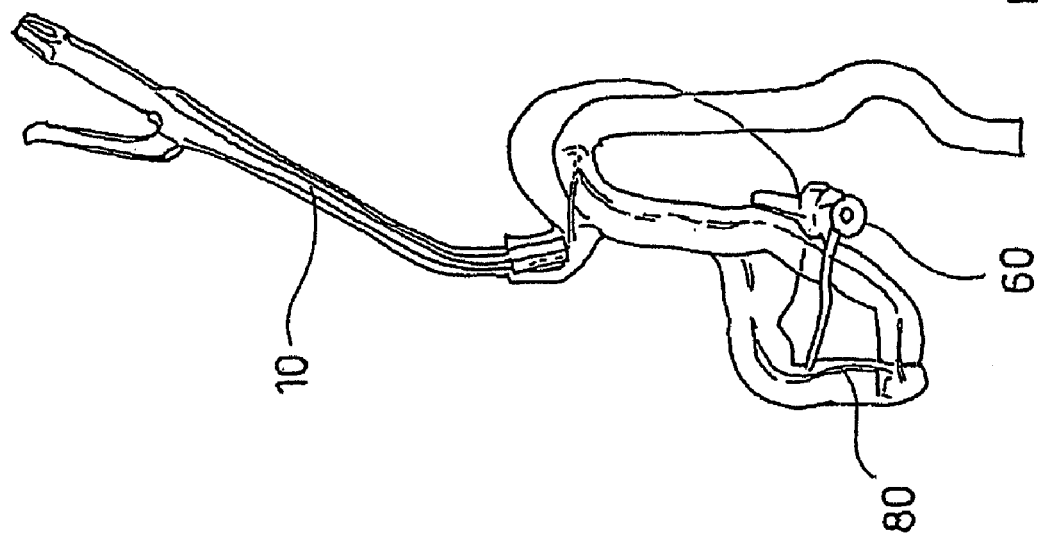

FIG. 29 illustrates a step which has been indicated as the step 13, in which the traction on the stomach end 80b of the guide wire is maintained in order to maintain the portions A and A' near each other. Furthermore, a circular stapler 10 is caused to slide on the guide wire from the stomach end 80b until it reaches the inside of the stomach, and until the stem 18 of the anvil 16 connects to the end of the stem 14 of the stapler 10 (such as illustrated in greater detail in FIGS. 2a and 41-44). The stapler 10 carries out the anastomosis between the portion A and the portion A' by cutting and suturing the tissue in a circular manner. A passage 84 is thereby formed (FIG. 30) which directly communicates the stomach and jejunum. When a positioning device 24 is used, the passage 84 is obtained by detaching the proximal component from the distal component and releasing the elastic ring 52 riding both enterostomies.

When the gastrojejunostomy (G-J) has been completed, the guide wire 66 is removed by drawing one end thereof.

With reference to the above example, FIG. 30-40 illustrate a jejunojejunostomy (J-J) step that is advantageously carried out by introducing guide or rail means through a natural orifice (such as the esophagus or mouth). Subsequently, the guide means, a guide wire in this case, form an open ring crossing the points of the tissues to be joined.

Figure 30:
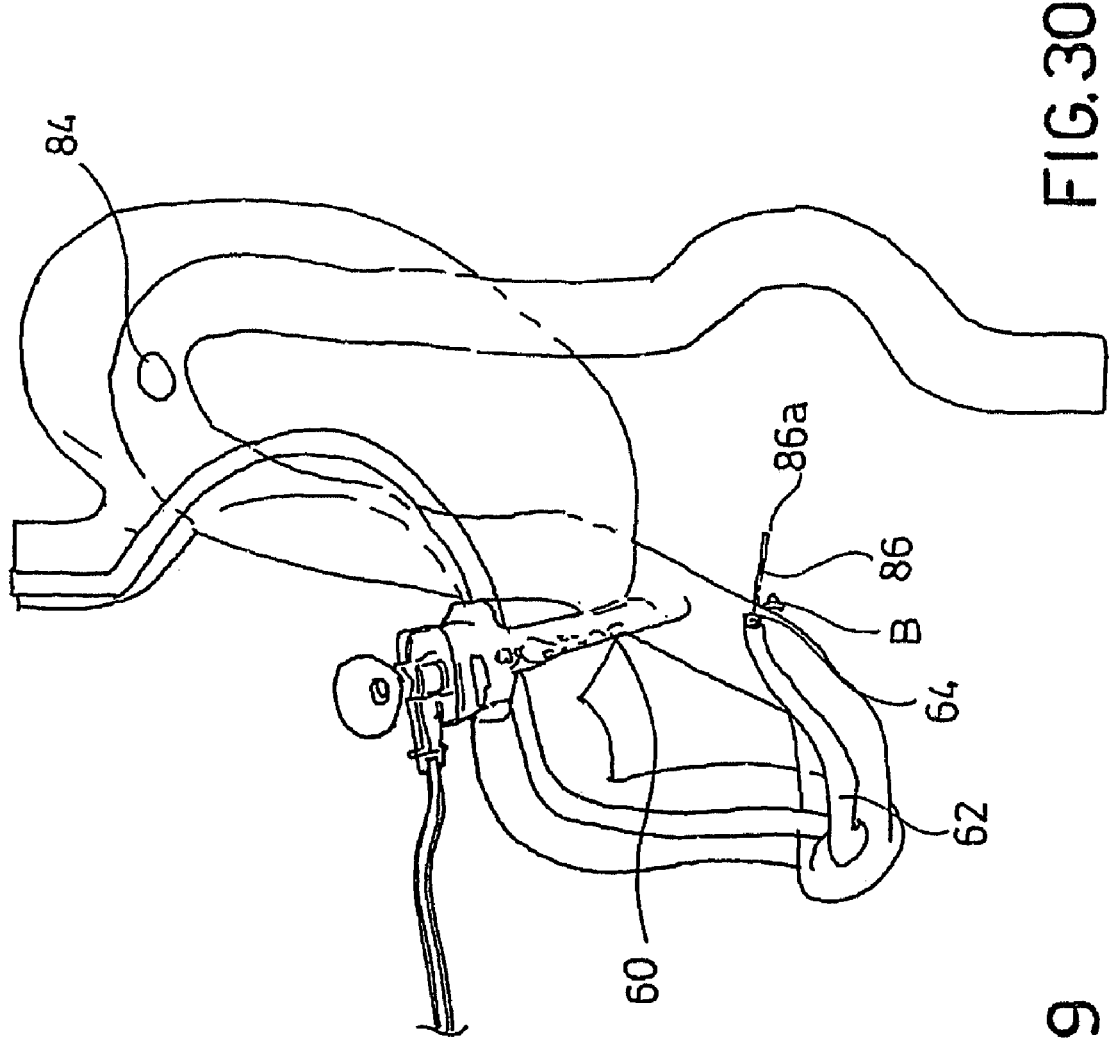

FIG. 30 illustrates a step designated as the step 14, in which a substantially conventional gastroscope 62 is introduced through the esophagus, stomach, passing through the pylorus and subsequently the duodenum to reach the jejunum. Particularly, the gastroscope 62 is advanced to a portion to be joined that is designated with B in order to carry out a proximal jejunostomy, which portion is proximally arranged relative to channel 84 (anastomosis) that has already been created.

A guide wire 86, or main guide wire, intended to form the open ring is advanced along a channel 64. The guide wire is advanced until a pointed end 86a thereof or a needle sliding within the guide wire protrudes from the gastroscope. The end 86a of the guide wire 66 perforates the jejunum wall from the inside and creates a jejunostomy (proximal enterostomy).

The laparoscope 60 is optionally provided. When this is provided, the guide wire 86 is advanced and the jejunostomy is created under the laparoscope visual control.

The jejunostomy can be carried out by pushing the guide wire directly through the jejunum wall. Alternatively, or in addition thereto, radiofrequency energy may be applied to perforate the jejunum wall and then advance the guide wire 86.

In other words, a guide wire 86 being part of guide or rail means which will be subsequently indicated in greater detail, is positioned within the tissue to be joined and passed through one of the tissue portions B to be joined (proximal jejunostomy).

Figure 31:
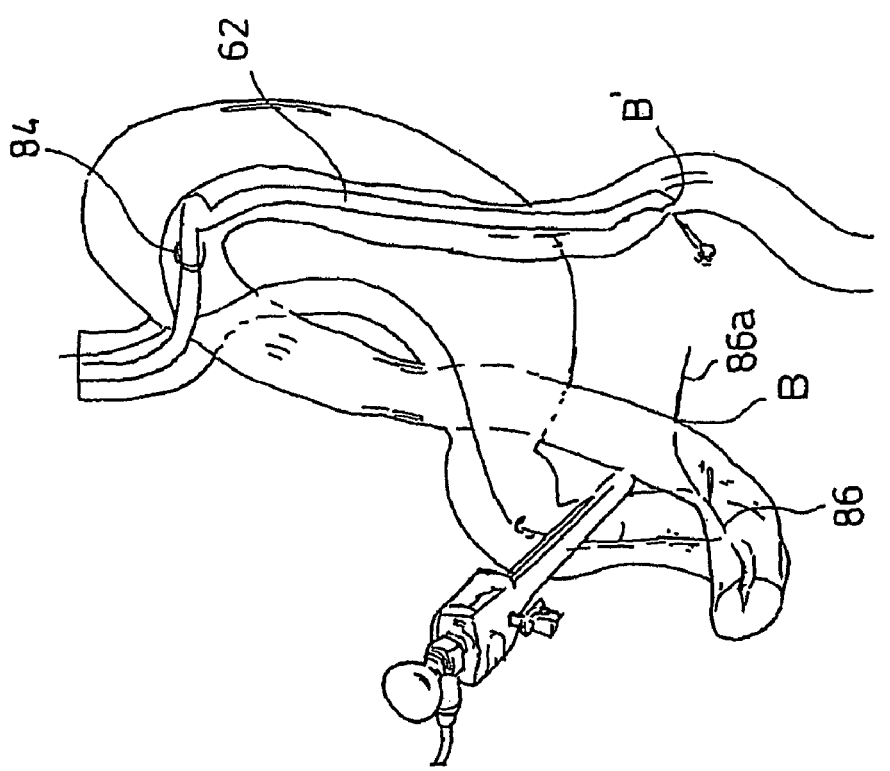

FIG. 31 illustrates a step which has been indicated as the step 15, in which the gastroscope 62 is removed and the guide wire 86 is left within the stomach and jejunum, with the end 86a protruding from the walls of the jejunum (proximal jejunostomy). The gastroscope 62 is then advanced through the stomach, the previously accomplished gastrojejunostomy (step 84) and a tract of the distal jejunum until a sufficient distance to create the jejunumjejunum (J-J) anastomosis. The latter portion has been indicated with the reference B'. Analogously to FIGS. 21 and 22 (steps 5 and 6) a secondary guide wire is advanced along the gastroscope 62 until a pointed end thereof protrudes from the end of the gastroscope 62. This pointed end is then passed through the tissue walls at the portion B' in order to create a distal jejunostomy. The distal jejunostomy can be also carried out either by directly pushing the pointed end through the jejunum wall or applying radiofrequency energy in order to perforate the wall, subsequently advancing the guide wire.

The creation of the distal jejunostomy can be monitored through the laparoscope.

A catheter with balloon-end may be optionally inserted along the gastroscope. When the balloon end is near the distal jejunostomy, the balloon is inflated in order to dilate the distal jejunostomy and the gastroscope is pushed in the abdominal cavity. This dilation may be required when the laparoscope is not used and monitoring is carried out through the gastroscope such that the latter can view the end 86*a* of the guide wire 86.

Figure 32:
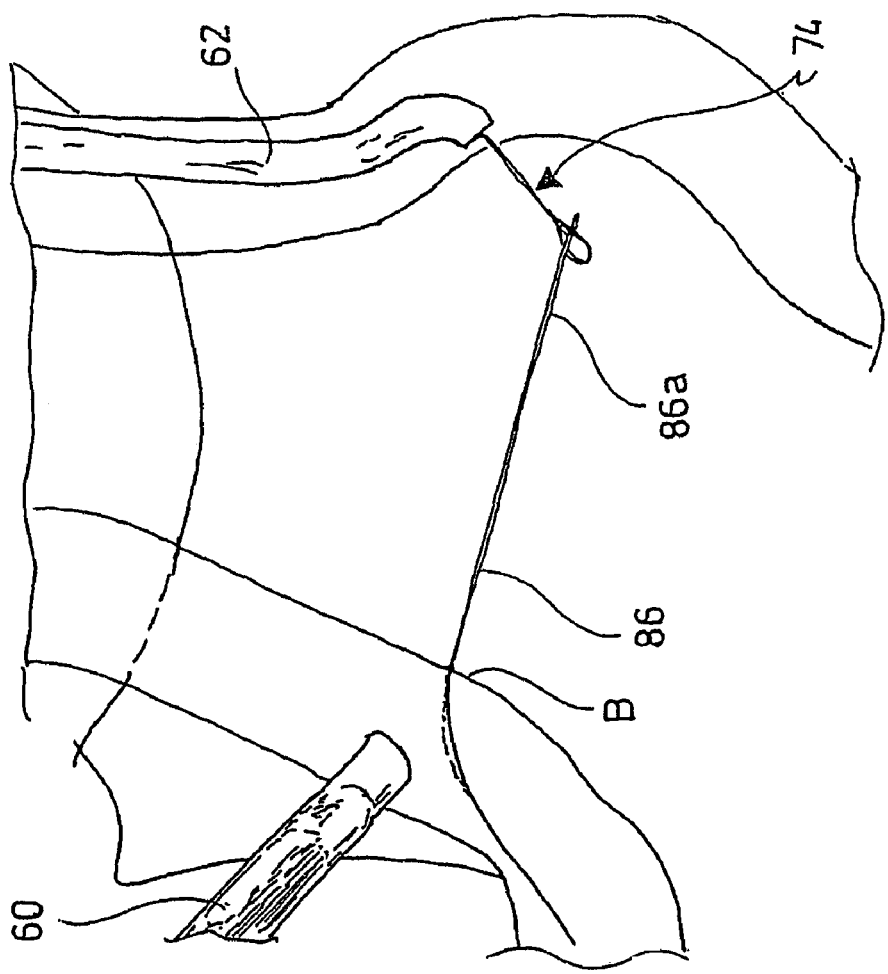

FIG. 32 illustrates a step which has been designated as the step 16, in which a gripping device 74 (endoscopic forceps or the like) similar to the one used in step 8, is advanced through the gastroscope to lock the end 86*a* of the main guide wire 86 protruding from the proximal jejunostomy site. Gripping the guide wire end is not required.

Figure 33:
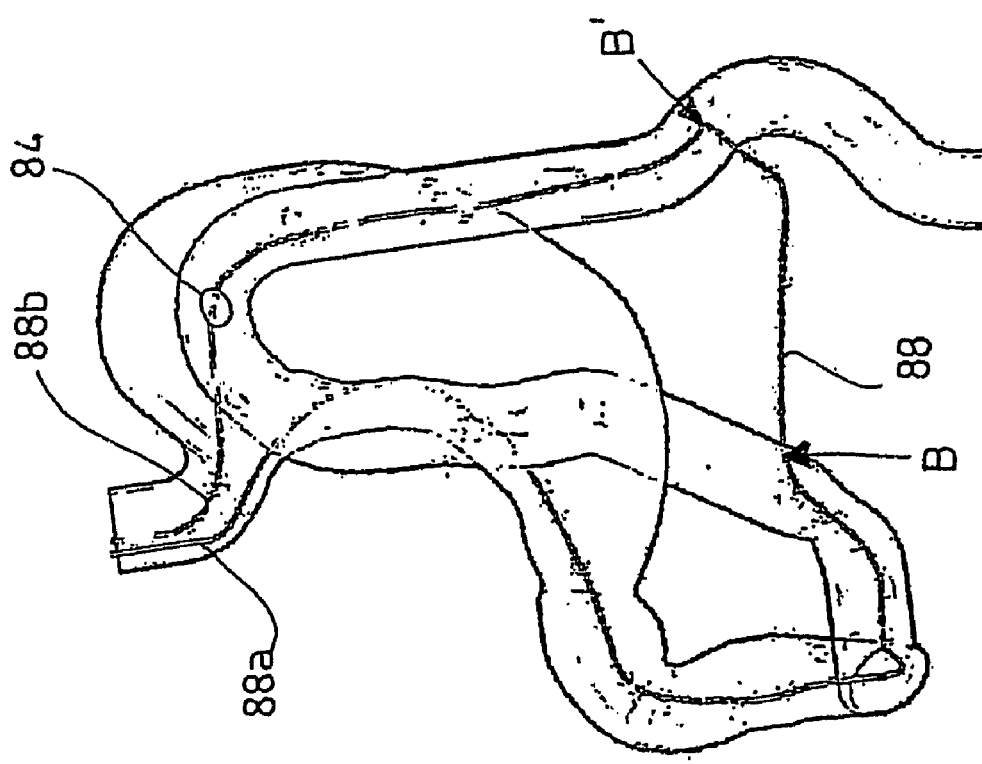

FIG. 33 illustrates a step which has been indicated as the step 17, in which the gastroscope has been removed and the main guide wire 86 has been pulled through the distal jejunostomy to form a ring 88 open at the ends thereof, or jejunumjejunum ring (the ring 2), the ends thereof protruding from the orifice used. In FIG. 33 the end of the jejunum, i.e. the end passing through the stomach and the jejunum and protruding therefrom at portion B has been designated with 88*a*, whereas the end of the stomach, i.e. the end passing through the stomach, protruding from the gastrojejunostomy (passage 84) and protruding from the jejunum at portion B' has been designated with 88*b*.

The ring 88 can be now used as a guide means or rail system in order to introduce and carry suitable anastomotic devices suitable to draw the tissues together and carry out the anastomosis in the site of interest (J-J). As described above, the anastomotic device is locked on the guide wire, an end thereof being pulled in order to advance the anastomotic device.

Figure 34:
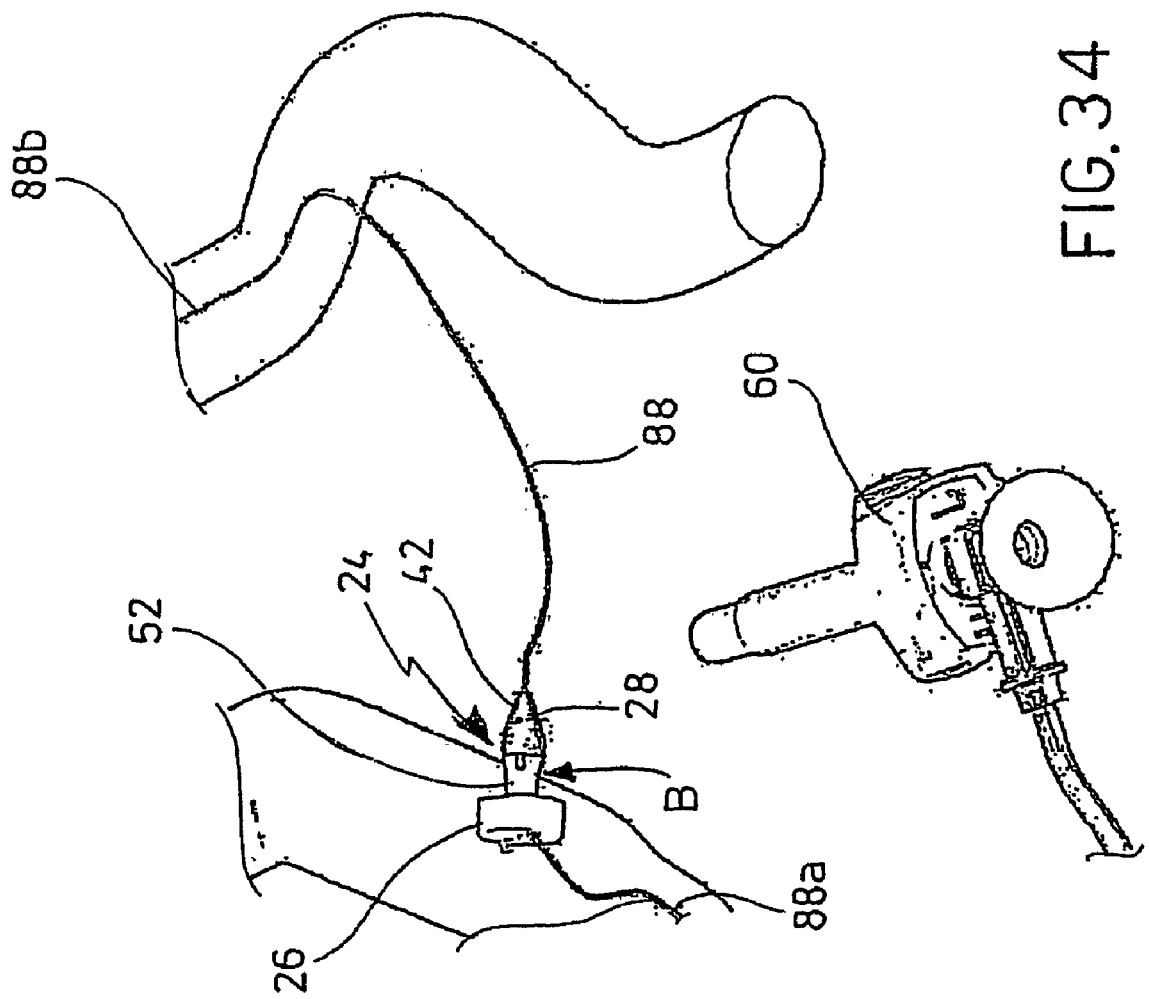

FIG. 34 illustrates a step which has been designated as the step 18, wherein an anastomotic device such as a positioning device 24 is inserted from the jejunum end 88*a* and pulled along the ring 88 of guide wire through the esophagus, stomach, duodenum and jejunum. The operation may be carried out under laparoscopic and/or gastroscopic control in order to view the movement.

The anastomotic device may be caused to slide on the guide wire from the jejunum end 88*a*. Traction is permitted due to an anchoring ring similar to that described above, which is made integral with the guide wire pushing against the proximal part of the selected anastomotic device. By pulling the guide wire from the end of stomach 88*b*, the anastomotic device can be pulled until the portion B of the jejunum.

As illustrated in FIG. 34, the positioning device 24 (channel 50 and cavity 38) is inserted on the end 88*a* of the guide wire from the side of the distal component 28.

The anastomotic device and particularly the positioning device 24 is pulled until it has partially passed the proximal jejunostomy. The head 42 of the distal component 28 and a part of the elastic ring 52 cross the proximal jejunostomy and protrude in the abdominal cavity, whereas the other part of the elastic ring 52 remains within the jejunum. The proximal component also remains within the jejunum and abuts, for example with the surface 26*a*, against the tissue wall to act as a striker.

FIG. 35 illustrates a step which has been designated as the step 19, in which the two jejunum branches are drawn together, optionally under gastroscopic and/or laparoscopic vision by keeping on pulling the anastomotic device (positioning device 24).

Particularly, the head 42 of the distal component 28 with a part of the elastic ring 52 penetrate in the distal jejunostomy.

Figure 37:
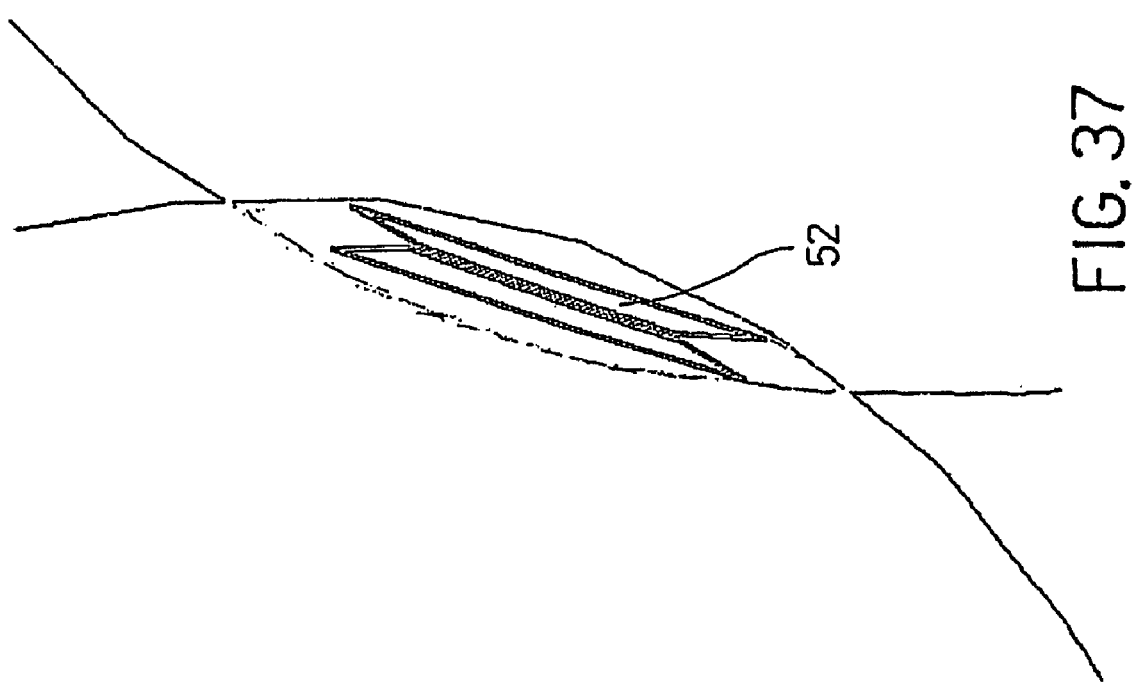

FIG. 36 illustrates a step which has been designated as the step 20, in which the elastic ring 52 that takes its uncompressed configuration, such as illustrated enlarged for example in FIG. 37 (step 21) is positioned. The ends of the elastic ring 52 fold between the proximal jejunostomy and the distal jejunostomy thereby maintaining the portion B and portion B' joined to each other thereby creating a circular anastomosis. The elastic ring 52 can be released from the positioning device 24 by simultaneously uncoupling the distal and proximal components 26 and 28. Alternatively, one of the two components can be uncoupled by pulling the same while keeping unchanged the position of the elastic ring 52 relative to the anastomotic site.

To uncouple the distal component and the proximal component, one can use the suture threads protruding from the holes 40 of the proximal component 26 and the holes 46 of the distal component 28 by coupling them by means of a suitable tool inserted in a gastroscope 62. The suture stitches are thus gripping points for uncoupling the proximal and distal components of the positioning device 24 from each other.

During positioning, the enterostomy can be viewed by means of a gastroscope or laparoscope.

When the jejunojejunostomy (J-J) has been completed, the guide wire 86 is removed by drawing one end thereof.

Figure 38:
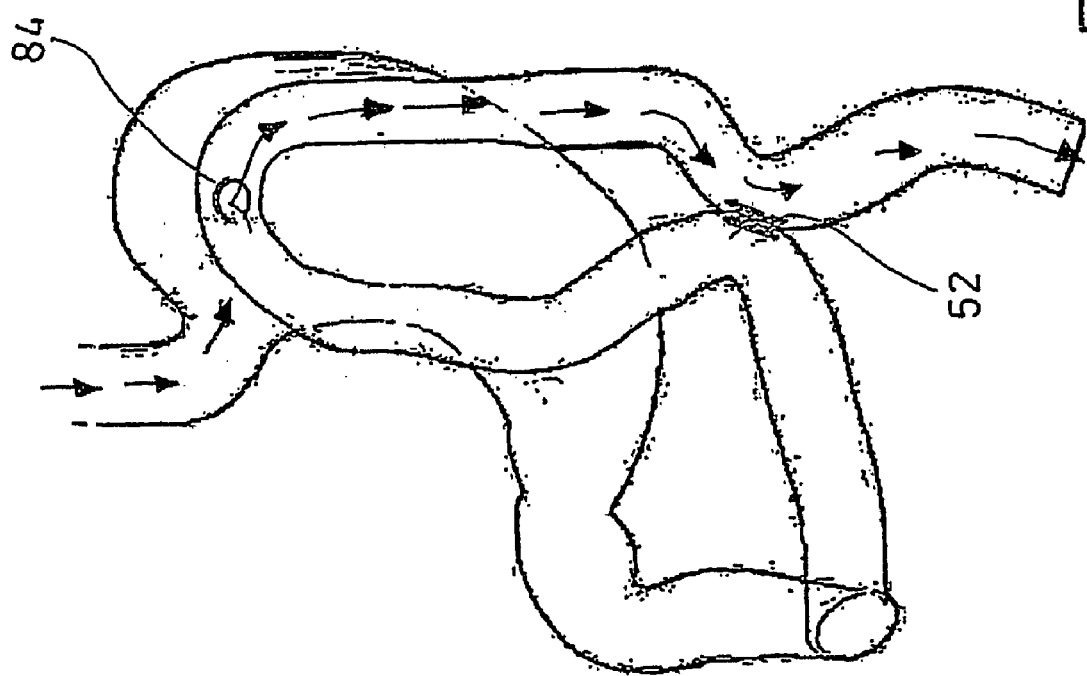

FIG. 38 illustrates a step which has been designated as the step 22, in which the gastrojejunostomy (G-J) and the jejunojejunostomy (J-J) have been completed and in which there is illustrated the route followed by the food along the digestive tract after it has been changed.

Figure 40:
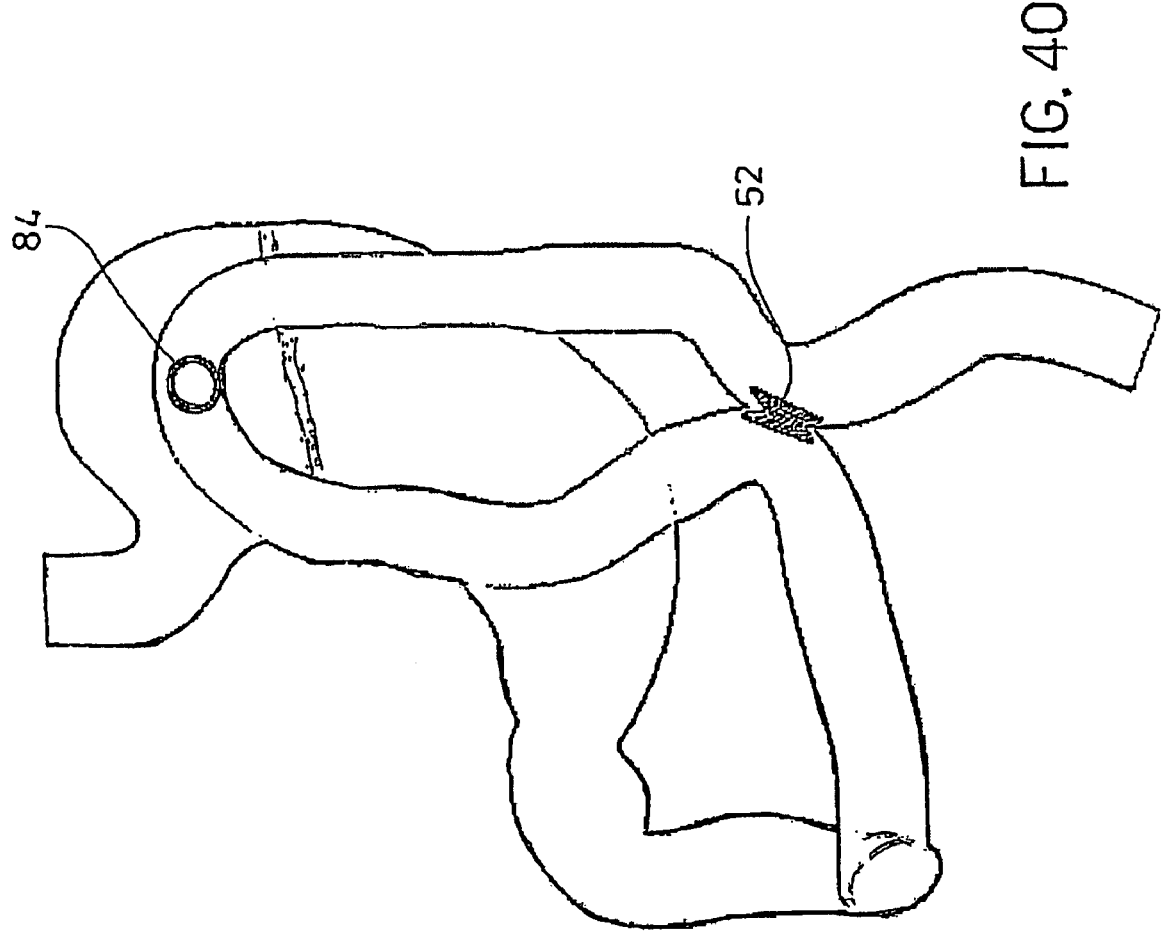
Figure 39:
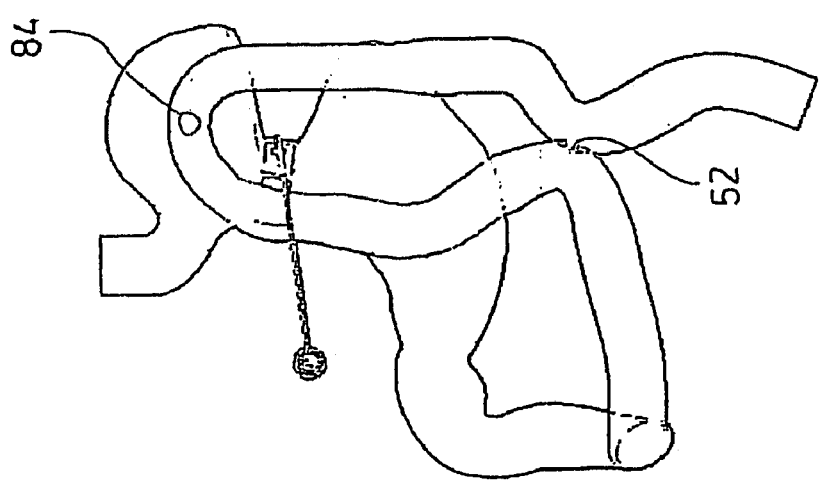
Figure 41:
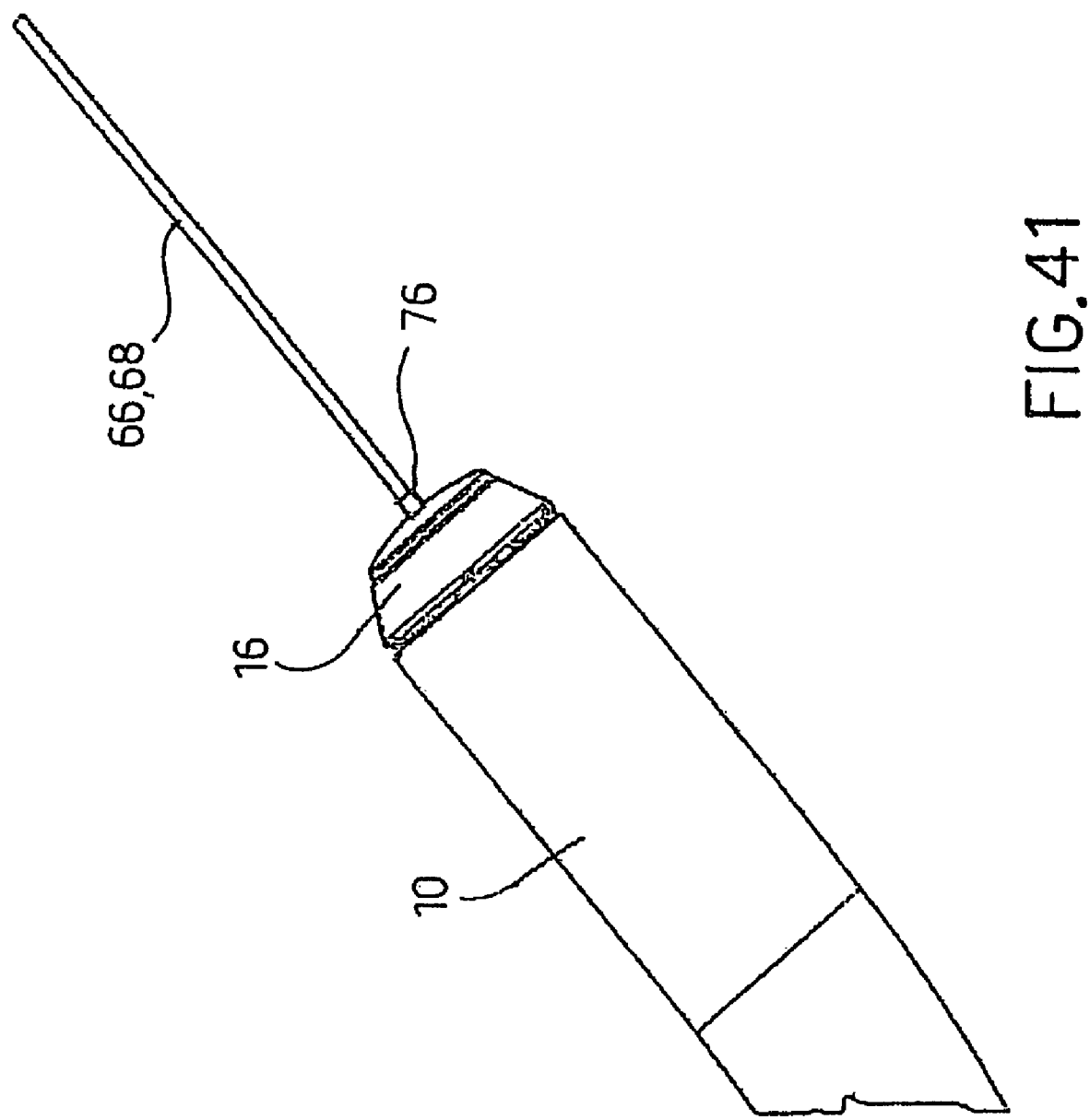
FIG. 41 illustrates a partial perspective view of a circular stapler, a positioning device and a guide wire, an anchoring ring being inserted thereon.
Figure 42:
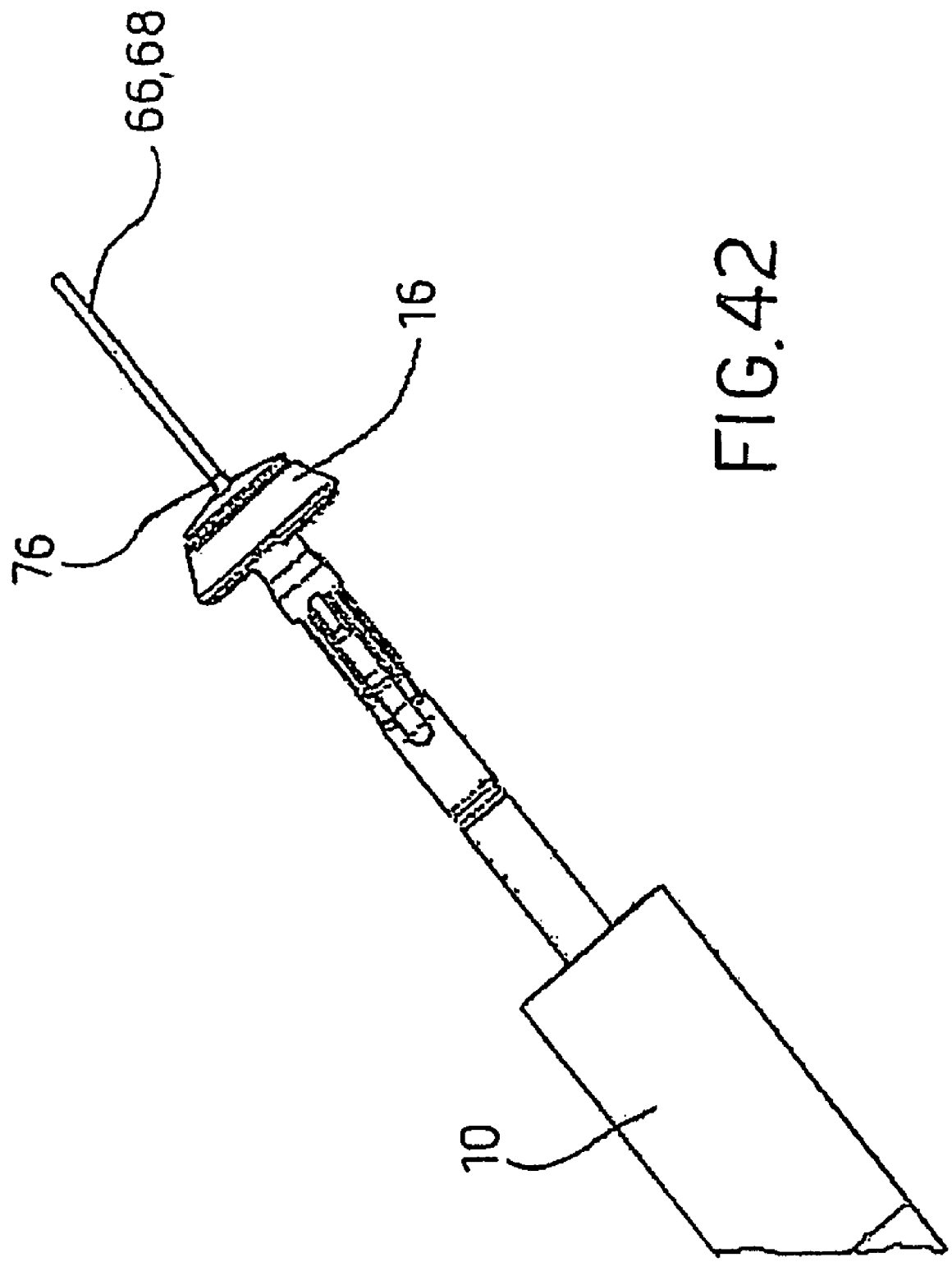
FIG. 42 illustrates the circular stapler, positioning device and guide wire from FIG. 41 while the positioning device is being inserted in the circular stapler.
Figure 43:
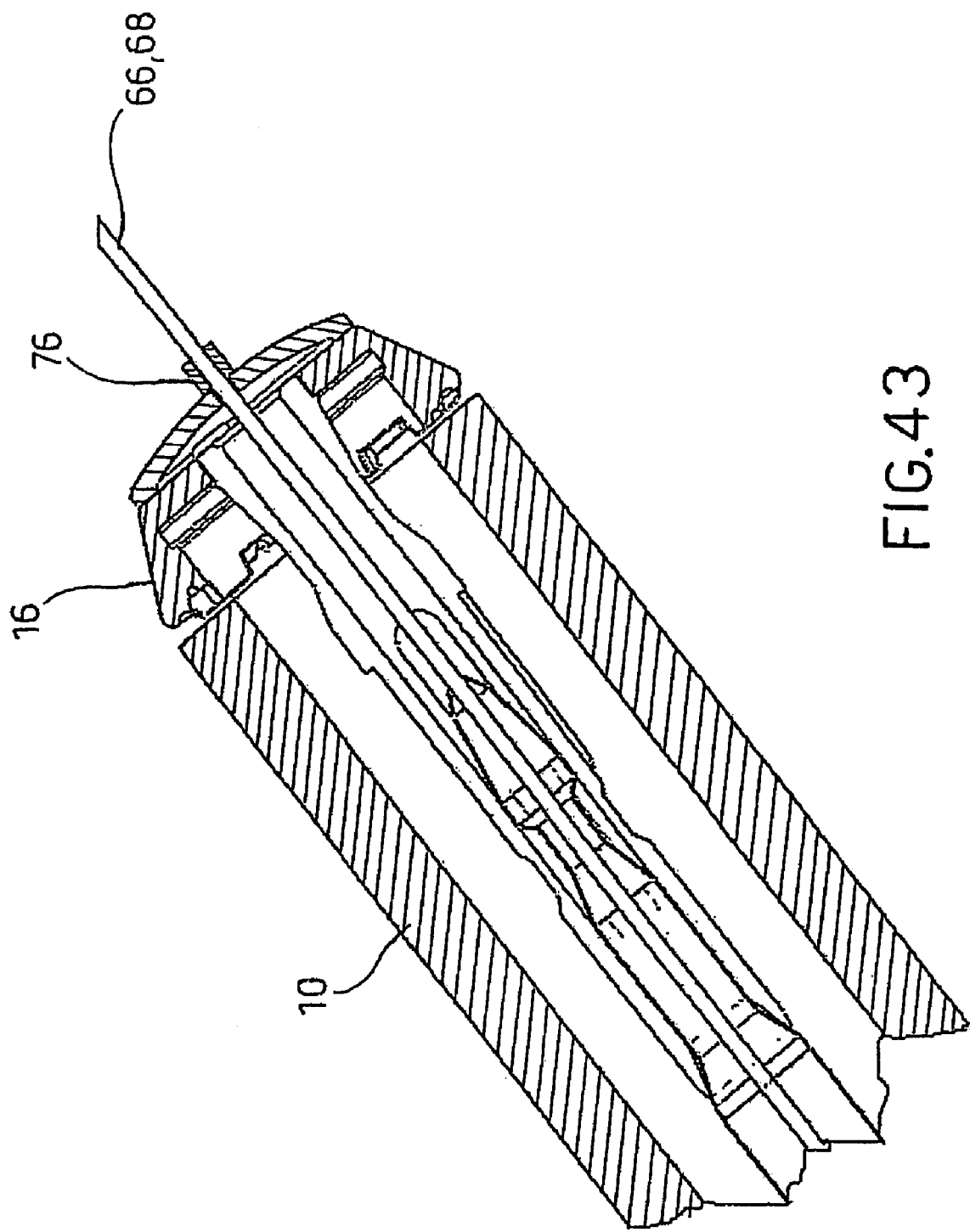
FIG. 43 illustrates the FIG. 41 in a longitudinal section.
Figure 44:
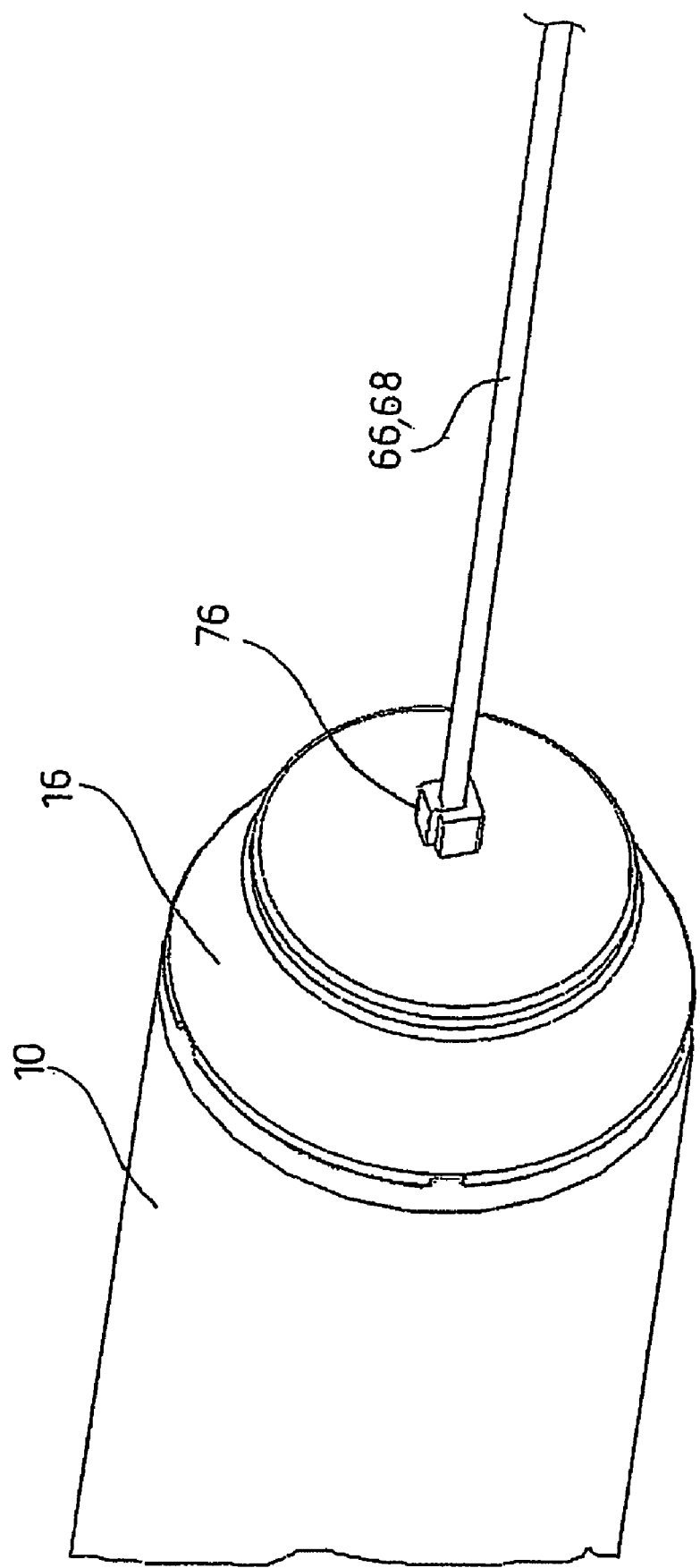
FIG. 44 illustrates FIG. 41 from a different point of view.

To complete the method discussed above, either a gastric partition obtained with a gastric bandage such as illustrated in FIG. 39 (step 23.1) or a gastric partition obtained with an endoscopic stapler such as illustrated in FIG. 40 (step 23.2) can be provided.

From what has been described above, one may appreciate how the provision of guide means carrying components or devices to the desired anastomotic site through natural orifices (such as the nose, mouth, ear, anus) or other luminal structures in order to carry out anastomosis greatly simplifies the procedure, shortens the patient's convalescence and eliminates the drawbacks of traditional surgery.

The provision of components and devices that suitably draw the tissue surfaces together and/or connect the surfaces by means of a passage is particularly advantageous and allows to carry out a completely endoluminal method.

It should be understood that variations and/or additions to what has been described and illustrated above may be provided.

In addition to the method described above, there may provided alternative procedures (ERCP, Chole duct, colo-proctostomy, jejunum-colostomy).

The order of the steps of the method illustrated in the annexed drawings and described above, (gastrojejunostomy or G-J, jejunojejunostomy or J-J, sectioning) can be readapted. For example, with patients that have already been subjected to gastric bandage, the steps G-J and J-J can be completed as described above. Subsequently, the gastric bandage can be completely restricted by carrying out a gastric partition thereby completing the procedure.

Alternatively to the use of the circular stapler 10 and anvil 16, the gastrojejunostomy G-J according to the steps described above (FIG. 17-FIG. 29) can be carried out by means of a positioning device 24 as described above (similarly to the jejunojejunostomy J-J steps corresponding to FIG. 31-38).

To the preferred embodiment of the device, stapler or method described above, those skilled in the art, aiming at satisfying contingent and specific requirements, may carry out a number of modifications, adaptations and replacement of elements with others functionally equivalent, without however departing from the scope of the claims below.

The invention claimed is:

1. A method for carrying out anastomosis in tracts of the digestive tube comprising the steps of:
   introducing through a natural orifice a guide means into first and second tissues portions to be drawn near and joined and, subsequently
   inserting an anvil of a circular stapler along the guide means, securing said anvil with respect to said guide means and drawing said anvil by means of said guide means against said second tissue portion;
   drawing said first and said second tissue portions together by pulling on said guide means to move said anvil together with said second tissue portion towards said first tissue portion; and
   further including the step of introducing a secondary guide to create a distal opening by causing a needle to slide within a tubular structure of said secondary guide wire, said needle perforating the tissue.

2. The method according to claim 1, further including the step of creating a proximal opening and a distal opening by causing a needle to slide within a tubular structure of said guide means to perforate the tissue.

3. The method according to claim 1, further including the step of inserting a gripping device through said distal opening and gripping the end of the guide means with said gripping device.

4. A method for carrying out anastomosis in tracts of the digestive tube comprising the steps of:
   introducing through a natural orifice a guide means into first and second tissues portions to be drawn near and joined and, subsequently
   inserting an anvil of a circular stapler along the guide means, securing said anvil with respect to said guide means and drawing said anvil by means of said guide means against said second tissue portion;
   drawing said first and said second tissue portions together by pulling on said guide means to move said anvil together with said second tissue portion towards said first tissue portion; and further comprising a step of carrying out a gastrojejunostomy comprising the steps of:
   introducing the guide means through a natural orifice or other orifice within the stomach and jejunum, and
   shaping the guide means into a first open ring having first and second ends leading to said orifice, placing said first ring across a proximal opening and a distal opening, and actuating said first ring to create a gastrojejunostomy.

5. The method according to claim 4, wherein said guide means is introduced through the esophagus, stomach and a tract of the jejunum and is passed through the jejunum wall.

6. The method according to claim 5, wherein the further comprising the step of causing a needle to slide within a tubular structure of the guide means so as to perforate the tissue.

* * * * *